US009758477B2

United States Patent
Guo et al.

(10) Patent No.: US 9,758,477 B2
(45) Date of Patent: Sep. 12, 2017

(54) SULFAMOYLBENZAMIDE DERIVATIVES AS ANTIVIRAL AGENTS AGAINST HBV INFECTION

(71) Applicants: DREXEL UNIVERSITY, Philadelphia, PA (US); BARUCH S. BLUMBERG INSTITUTE, Doylestown, PA (US)

(72) Inventors: Ju-Tao Guo, Lansdale, PA (US); Xiaodong Xu, Doylestown, PA (US); Timothy M. Block, Doylestown, PA (US)

(73) Assignees: Drexel University, Philadelphia, PA (US); Baruch S. Blumberg Institute, Doylestown, PA (US)

( * ) Notice: Subject to any disclaimer, the term of this patent is extended or adjusted under 35 U.S.C. 154(b) by 0 days.

(21) Appl. No.: 14/975,239

(22) Filed: Dec. 18, 2015

(65) Prior Publication Data

US 2016/0101074 A1 Apr. 14, 2016

Related U.S. Application Data

(63) Continuation of application No. 14/130,140, filed as application No. PCT/US2012/044775 on Jun. 29, 2012, now Pat. No. 9,399,619.

(Continued)

(51) Int. Cl.
*A61K 31/55* (2006.01)
*A61K 31/47* (2006.01)
(Continued)

(52) U.S. Cl.
CPC .......... *C07C 311/46* (2013.01); *A61K 31/167* (2013.01); *A61K 31/18* (2013.01); *A61K 31/341* (2013.01); *A61K 31/4406* (2013.01); *A61K 31/4453* (2013.01); *A61K 31/5375* (2013.01); *A61K 31/54* (2013.01); *A61K 31/55* (2013.01); *A61K 31/553* (2013.01);
(Continued)

(58) Field of Classification Search
CPC ..... A61K 31/55; A61K 31/4453; A61K 31/18
USPC .................. 514/212.01, 603, 317
See application file for complete search history.

(56) References Cited

U.S. PATENT DOCUMENTS 3,055,905 A 9/1962 Schmid et al.
5,607,929 A 3/1997 Nicol et al.
(Continued)

FOREIGN PATENT DOCUMENTS

EP 2280001 A1 2/2011
GB 912060 12/1962
(Continued)

OTHER PUBLICATIONS

STN Registration No. 330461-34-2, 2001.*
(Continued)

*Primary Examiner* — Shengjun Wang
(74) *Attorney, Agent, or Firm* — Saul Ewing LLP; Kathryn Doyle; Domingos J. Silva

(57) ABSTRACT

The present invention provides sulfamoylbenzamide derivatives, and pharmaceutical compositions thereof. In certain embodiments, the compounds and pharmaceutical compositions of the invention inhibit pregenomic RNA encapsidation. In other embodiments, the compounds and pharmaceutical compositions of the invention are useful for treating Hepatitis B virus (HBV) infection.

2 Claims, 3 Drawing Sheets

Related U.S. Application Data

(60) Provisional application No. 61/503,830, filed on Jul. 1, 2011.

(51) Int. Cl.

| | |
|---|---|
| *A61K 31/18* | (2006.01) |
| *C07C 311/46* | (2006.01) |
| *A61K 31/341* | (2006.01) |
| *C07D 281/16* | (2006.01) |
| *C07D 295/26* | (2006.01) |
| *C07D 213/40* | (2006.01) |
| *C07D 307/52* | (2006.01) |
| *C07D 307/68* | (2006.01) |
| *C07D 211/96* | (2006.01) |
| *C07D 223/04* | (2006.01) |
| *A61K 31/167* | (2006.01) |
| *A61K 31/4406* | (2006.01) |
| *A61K 31/4453* | (2006.01) |
| *A61K 31/5375* | (2006.01) |
| *A61K 31/54* | (2006.01) |
| *A61K 31/553* | (2006.01) |
| *A61K 31/44* | (2006.01) |
| *A61K 31/541* | (2006.01) |
| *A61K 31/445* | (2006.01) |
| *A61K 31/5377* | (2006.01) |

(52) U.S. Cl.
CPC .......... *C07D 211/96* (2013.01); *C07D 213/40* (2013.01); *C07D 223/04* (2013.01); *C07D 281/16* (2013.01); *C07D 295/26* (2013.01); *C07D 307/52* (2013.01); *C07D 307/68* (2013.01); *A61K 31/44* (2013.01); *A61K 31/445* (2013.01); *A61K 31/5377* (2013.01); *A61K 31/541* (2013.01); *A61K 2300/00* (2013.01)

(56) References Cited

U.S. PATENT DOCUMENTS

| | | | |
|---|---|---|---|
| 5,939,423 | A | 8/1999 | Karlin et al. |
| 7,297,796 | B2* | 11/2007 | Dolle .................. C07C 311/16 546/205 |
| 2006/0079557 | A1 | 4/2006 | Dolle et al. |
| 2009/0163545 | A1 | 6/2009 | Goldfarb |
| 2009/0239830 | A1 | 9/2009 | Munger |
| 2009/0259044 | A1 | 10/2009 | Kazantsev et al. |
| 2010/0009970 | A1 | 1/2010 | Johansen |
| 2010/0009974 | A1 | 1/2010 | Francotte et al. |
| 2011/0009622 | A1 | 1/2011 | Jitsuoka et al. |

FOREIGN PATENT DOCUMENTS

| | | |
|---|---|---|
| GB | 921520 | 3/1963 |
| JP | H0959236 A | 3/1997 |
| WO | 9936398 A | 7/1999 |
| WO | 2008011476 A2 | 1/2008 |
| WO | 2008022171 A1 | 2/2008 |
| WO | 2009016088 A1 | 2/2009 |
| WO | 2009018219 A2 | 2/2009 |
| WO | 2010123139 A1 | 10/2010 |
| WO | WO2013006394 | 1/2013 |
| WO | WO2013096744 | 6/2013 |
| WO | WO2013130703 A2 | 9/2013 |

OTHER PUBLICATIONS

Akbar, S.M.F. et al., "Treatment Of Hepatitis B Virus-Infected Patients: Utility of Therapeutic Recommendations In Developing Countries," Expert Opin. Pharmacother. Jul. 2009, vol. 10, No. 10, pp. 1605-1614.

Billioud, G. et al., "The Main Hepatitis B Virus (HBV) Mutants Resistant to Nucleoside Analogs are Susceptible in vitro to Non-Nucleoside Inhibitors of HBV Replication," Antiviral Research, 2011, vol. 92, pp. 271-276.

Campagna, M.R. et al., "Sulfamoylbenzamide Derivatives Inhibit the Assembly of Hepatitis B Virus Nucleocapsids," Journal of Virology, 2013, vol. 87, No. 12, pp. 6931-6942.

Dienstag, J. "Benefits and Risks of Nucleoside Analog Therapy for Hepatitis B," Hepatology, 2009, vol. 49, No. S5 Suppl., S112-S121.

Janssen, H.L.A. et al., "Pegylated Interferon Alfa-2b Alone or in Combination with Lamivudine for HBeAg-positive chronic Hepatitis B: A Randomised Trial", www.thelancet.com, 2005, vol. 365, pp. 123-129.

Keeffe, E.B. et al., "A Treatment Algorithm for the Management of Chronic Hepatitis B Virus Infection in the United States: 2008 Update", Clinical Gastroenterology and Hepatology, 2008, vol. 6, pp. 1315-1341.

Lau, G.K.K. et al., "Peginterferon Alfa-2a, Lamivudine, and the Combination for HBeAg-Positive Chronic Hepatitis B," The New England Journal of Medicine, 2005, vol. 352, No. 26, pp. 2682-2695.

Lee, W., "Hepatitis B Virus Infection," The New England Journal of Medicine, 1997, vol. 337, No. 24, pp. 1733-1745.

Liaw, Y-F., "Antiviral Therapy of Chronic Hepatitis B: Opportunities and Challenges in Asia," Journal of Hepatology, 2009, vol. 51, pp. 403-410.

Lok, A.S.F., "Prevention of Hepatitis B Virus-Related Hepatocellular Carcinoma," Gastroenterology, 2004, vol. 127: S303-S309.

McMahon, B.J., "Epidemiology and Natural History of Hepatitis B," Seminars in Liver Disease, 2005, vol. 25, Supplement 1, pp. 1-8.

Perrillo, R., "Benefits and Risks of Interferon Therapy for Hepatitis B," Hepatology, 2009, vol. 49, pp. S103-S111.

Peters, M.G., "Special Populations with Hepatitis B Virus Infection," Hepatology, 2009, vol. 49, No. 5, pp. S146-S155.

Zoulim, F. et al., "Hepatitis B Virus Resistance to Nucleos(t)ide Analogues," Gastroenterology, 2009, vol. 137, pp. 1593-1608.

International Search Report dated Sep. 11, 2012, for International Patent Application No. PCT/US2012/044775.

El-Sharief, A.A. et al., "Synthesis of Different Types of Chlorinated Sulfonamides with Expected Insecticidal and Bactericidal Activities," Proceedings of the Indian National Science Academy. Part A. Physical Sciences, Indian National Science Academy, 1987, vol. 53, No. 1, pp. 179-188.

Ermann, M. et al., "Arylsulfonamide CB2 Receptor Agonists: SAR and Optimization of CB2 Selectivity," Bioorganic & Medicinal Chemistry Letters, 2008, vol. 18, No. 5, pp. 1725-1729.

Kim, N.D. et al., "Discovery of Novel HCV Polymerase Inhibitors Using Pharmacophore-based Virtual Screening," Bioorganic & Medicinal Chemistry Letters, 2011, vol. 21, No. 11, pp. 3329-3334.

Lambeng, N. et al., "Arylsulfonamides as a New Class of Cannabinoid CB1 Receptor Ligands: Identification of a Lead and Initial SAR Studies," Bioorganic & Medicinal Chemistry Letters, 2006, vol. 17, No. 1, pp. 272-277.

Taylor, D.M. et al., "A Brain-Permeable Small Molecule Reduces Neuronal Cholesterol by Inhibiting Activity of Sirtuin 2 Deacetylase," ACS Chemical Biology, 2011, vol. 6, No. 3, pp. 540-546.

Kansal, et al., "A Three Dimensional Pharmacophore Modeling for KDR and Tie-2 Receptor Tyrosine Kinase Inhibitors and Virtual Screening for New Multikinase Inhibitors", QSAR Comb Sci, vol. 28, No. 10, 2009, pp. 1130-1147.

Kushner, et al., "Anticonvulsants. N-Benzylamides", Journal of Organic Chemistry, vol. 16, 1951, pp. 1283-1288.

Mohamed, et al., "Synthesis of Different types of Chlorinated Sulphonamides with Expected Insecticidal and Antimicrobial Activities", Acta Pharm. Jugosl., vol. 36, No. 3, 1986, pp. 301-310.

Outeiro, et al., "Sirtuin 2 Inhibitors Rescue alpha-synuclein-mediated Toxicity in Models of Parkinson's Disease", Science, vol. 317, No. 5837, 2007, pp. 516-519.

(56) References Cited

OTHER PUBLICATIONS

Petrow, et al., "Studies in the Field of Diuretic Agents, Part VII: 4-chloro-2'-methyl-3-sulphamoylbenzanilide", Journal of Pharmacy and Pharmacology, 15(2), 1963, pp. 138-148.

* cited by examiner

SULFAMOYLBENZAMIDE DERIVATIVES AS ANTIVIRAL AGENTS AGAINST HBV INFECTION

CROSS-REFERENCE TO RELATED APPLICATIONS

The present application is a continuation of, and claims priority to, U.S. patent application Ser. No. 14/130,140, filed Mar. 18, 2014, which is the U.S. national phase application filed under 35 U.S.C. §371 claiming priority to International Patent Application No. PCT/US2012/044775, filed Jun. 29, 2012, which claims priority under 35 U.S.C. §119(e) to U.S. Provisional Patent Application No. 61/503,830, filed Jul. 1, 2011, all of which are hereby incorporated by reference in their entireties herein.

FIELD OF INVENTION

The present invention describes compounds and methods useful as pregenomic RNA encapsidation inhibitors, useful for the treatment of Hepatitis B virus (HBV) infection and related conditions.

BACKGROUND OF THE INVENTION

Hepatitis B virus (HBV) infection remains a major public health problem. Currently, an estimated 350 million people worldwide and 1.4 million in the US are chronically infected with HBV (McMahon, 2005). Approximately one-third of these individuals will die from serious liver diseases, such as cirrhosis and hepatocellular carcinoma, if left untreated (Lee, 1997; Lok, 2004).

Seven drugs are currently available for the management of chronic hepatitis B, which include two formulations of alpha-interferon (standard and pegylated) and five nucleos(t)ide analogues (lamivudine, adefovir, entecavir, telbivudine, and tenofovir) that inhibit HBV DNA polymerase (Keeffe et al., 2008). At present, the preferred first-line treatment choices are entecavir, tenofovir or peg-interferon alfa-2a. However, even with the first-line treatment options, peg-interferon alfa-2a is effective in achieving certain serological milestones in only one-third of treated patients and frequently associated with severe side effects (Janssen et al., 2005; Lau et al., 2005; Perrillo, 2009). Entecavir and tenofovir are highly potent HBV inhibitors, but a long-term or possibly life-time treatment is required to continuously suppress HBV replication, which may eventually fail due to emergence of drug resistant viruses (Dienstag, 2009). Hence, there is a pressing need for the introduction of novel, safe and effective therapies for chronic hepatitis B, which is listed by National Institute of Allergy and Infectious Diseases (NIAID) as a High Priority Area of Interest.

HBV is a noncytopathic, liver tropic DNA virus belonging to Hepadnaviridae family. Pregenomic (pg) RNA is the template for reverse transcriptional replication of HBV DNA and its encapsidation, together with viral DNA polymerase, into nucleocapsid is essential for the subsequent viral DNA synthesis. Inhibition of pregenomic RNA (pg) encapsidation would block HBV replication and provide a new therapeutic approach to the treatment of HBV.

Clinically, inhibition of pregenomic RNA (pg) encapsidation offers the following therapeutic advantages: First, inhibition of pregenomic RNA (pg) encapsidation will complement the current medications by providing an additional option for a subpopulation of patients that do not tolerate or benefit from the current medications (Akbar et al., 2009; Liaw, 2009; Peters, 2009; Wiegand, van Bommel, and Berg). Second, based on their distinct antiviral mechanism, inhibition of pregenomic RNA (pg) encapsidation will be effective against HBV variants that are resistant to the currently available DNA polymerase inhibitors (Zoulim and Locarnini, 2009). Third, like the Highly Active Antiretroviral Therapy (HAART) for human immunodeficiency virus (HIV) infection (Este and Cihlar), combination therapy of the inhibitors of pregenomic RNA (pg) encapsidation with DNA polymerase inhibitors should synergistically suppress HBV replication and prevent the emergence of drug resistance and thus offers a safer and more effective treatment for chronic hepatitis B infection.

There is a long felt need for new antiviral drugs that are both disease-modifying and effective in treating patients that are infected with hepatitis B virus. There is also a clear and present need for new antiviral drugs that are both disease modifying and effective in treating patients that are infected with drug resistant hepatitis B virus. The present invention addresses the need for new antiviral drugs that are both disease-modifying and effective in treating patients that are infected with hepatitis B virus.

BRIEF SUMMARY OF THE INVENTION

The present invention is directed toward the novel method of use of sulfamoylbenzamide derivatives of the formula (I), useful as pregenomic RNA encapsidation inhibitors of HBV for the treatment of Hepatitis B virus (HBV) infection and related conditions.

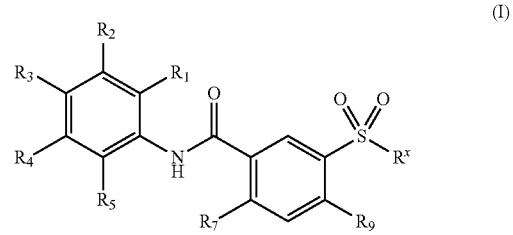

(I)

Including hydrates, solvates, pharmaceutically acceptable salts, prodrugs and complexes thereof, wherein:

$R^1$ is hydrogen;
$R^2$ is selected from a group consisting of hydrogen, methyl, trifluoromethyl, fluorine, and chlorine;
$R^3$ is selected from a group consisting of hydrogen, methyl, fluorine, and chlorine:
$R^4$ is selected from a group consisting of hydrogen, fluorine, chlorine, and methyl;
$R^5$ is selected from a group consisting of hydrogen and chlorine;
$R^7$ is selected from a group consisting of hydrogen, chlorine, fluorine, and bromine;
$R^9$ is selected from a group consisting of hydrogen, methyl, fluorine, and chlorine;
$R^x$ is selected from a group consisting of $NH_2$,

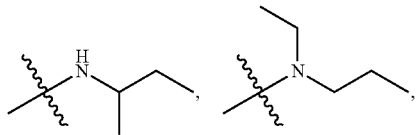

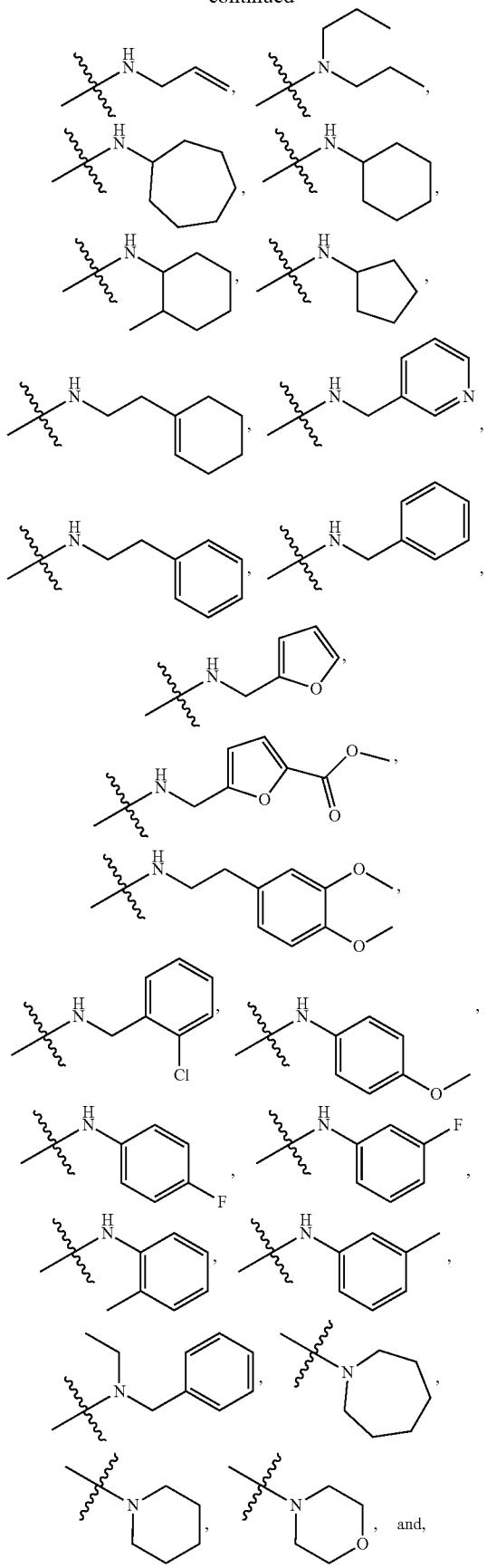

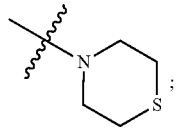

The present invention is further directed toward the novel method of use of sulfamoylbenzamide derivatives of the formula (II), useful as pregenomic RNA encapsidation inhibitors of HBV for the treatment of Hepatitis B virus (HBV) infection and related conditions.

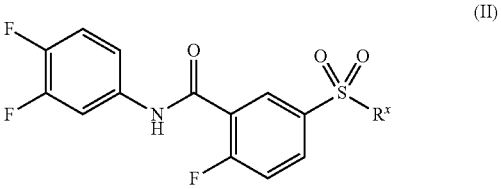

Including hydrates, solvates, pharmaceutically acceptable salts, prodrugs and complexes thereof, wherein:

$R^x$ is selected from a group consisting of

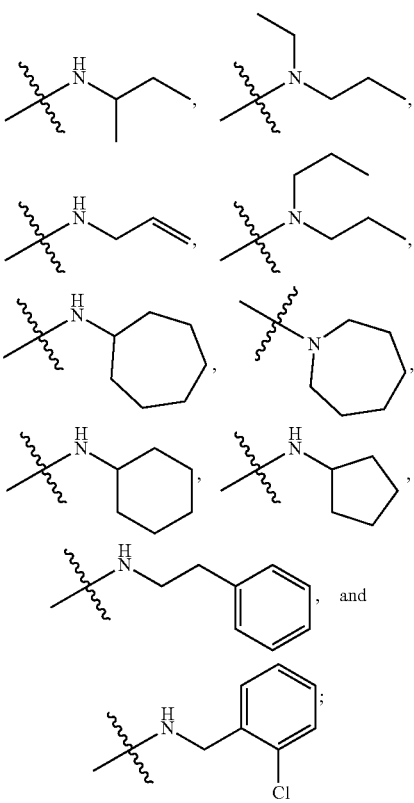

The present invention is further directed toward the novel method of use of sulfamoylbenzamide derivatives of the formula (III), useful as pregenomic RNA encapsidation inhibitors of HBV for the treatment of Hepatitis B virus (HBV) infection and related conditions.

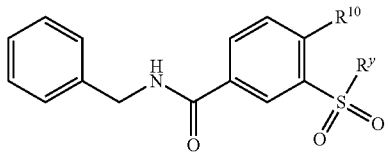

Including hydrates, solvates, pharmaceutically acceptable salts, prodrugs and complexes thereof, wherein:
$R^{10}$ is selected from a group consisting of hydrogen, methyl, chlorine, and bromine;
$R^y$ is selected from a group consisting of

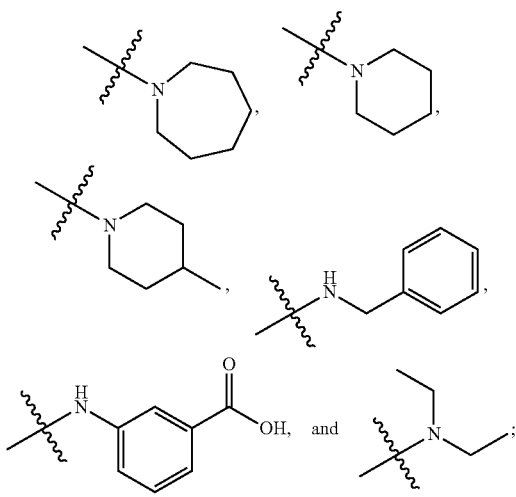

The present invention is further directed toward the novel method of use of sulfamoylbenzamide derivatives of the formula (IV), useful as pregenomic RNA encapsidation inhibitors of HBV for the treatment of Hepatitis B virus (HBV) infection and related conditions.

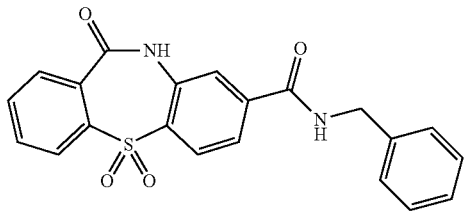

Including hydrates, solvates, pharmaceutically acceptable salts, prodrugs and complexes thereof.

The present invention further relates to compositions comprising:
an effective amount of one or more compounds according to the present invention and an excipient.

The present invention also relates to a method for treating or preventing diseases that involve pregenomic RNA encapsidation, including, for example, HBV infection, said method comprising administering to a subject an effective amount of a compound or composition according to the present invention.

The present invention yet further relates to a method for treating or preventing diseases that involve pregenomic RNA encapsidation, including, for example, HBV infection, wherein said method comprises administering to a subject a composition comprising an effective amount of one or more compounds according to the present invention and an excipient.

The present invention also relates to a method for treating or preventing disease or conditions associated with HBV infection, and diseases that involve pregenomic RNA encapsidation. Said methods comprise administering to a subject an effective amount of a compound or composition according to the present invention.

The present invention yet further relates to a method for treating or preventing disease or conditions associated with HBV infection, and diseases that involve pregenomic RNA encapsidation, wherein said method comprises administering to a subject a composition comprising an effective amount of one or more compounds according to the present invention and an excipient.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

Figure 1:
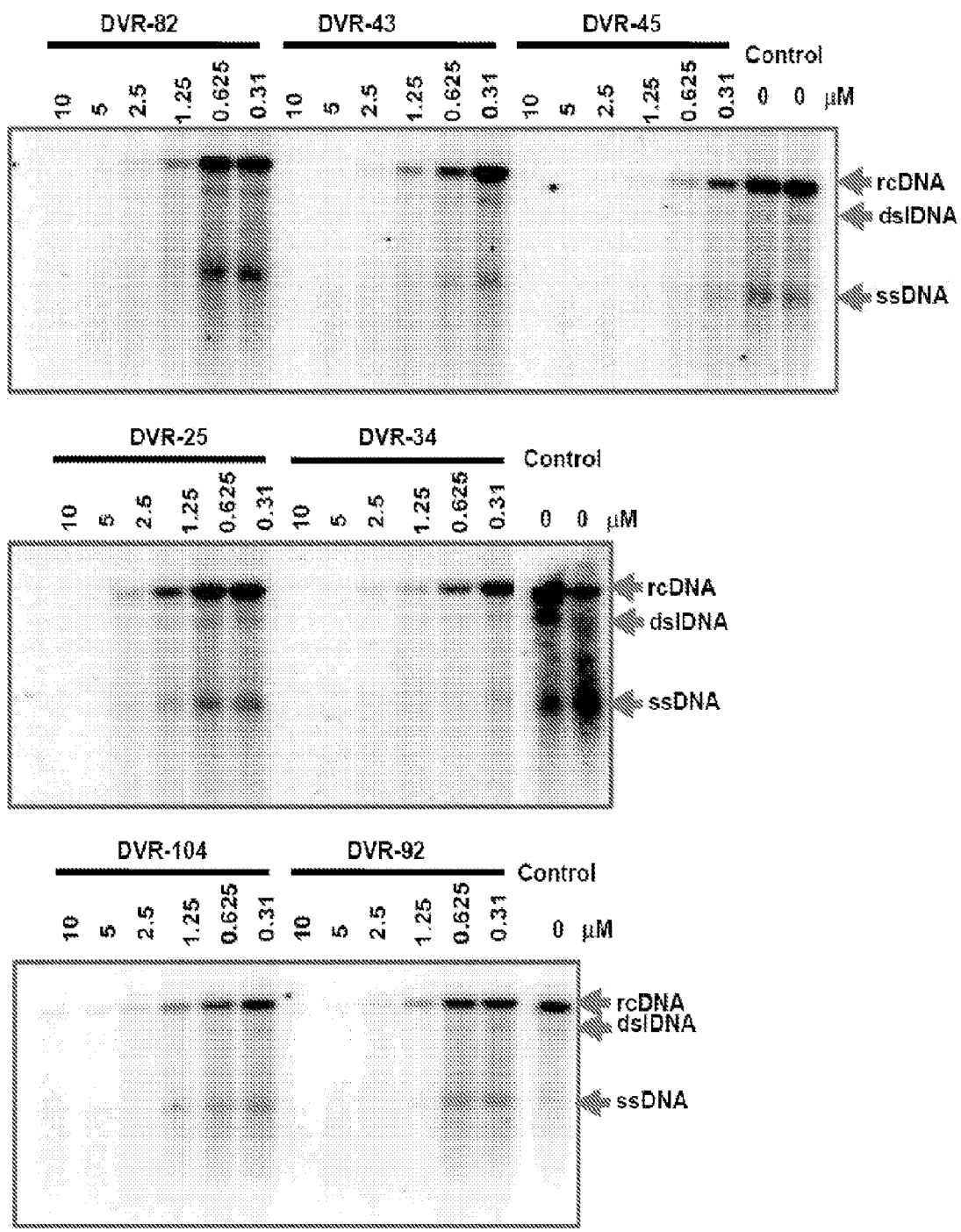
FIG. 1: Effects of the selected compounds of the present invention on HBV DNA replication in HepDES19 cells. HepDES19 cells were left untreated (control) or treated with the indicated concentrations of the compounds of the disclosure for 6 days. Intracellular nucleocapsid-associated HBV DNA was extracted and resolved in 1.5% agarose gel by electrophoresis and determined by Southern blot hybridizations. Abbreviations: rcDNA: relaxed circular DNA; dslDNA: double-stranded linear DNA; ssDNA: single-stranded DNA

The pregenomic RNA encapsidation inhibitors of the present invention are capable of treating and preventing diseases associated with pregenomic RNA encapsidation, for example HBV infection. Pregenomic (pg) RNA is the template for reverse transcriptional replication of HBV DNA and its encapsidation, together with viral DNA polymerase, into nucleocapsid is essential for the subsequent viral DNA synthesis. Without wishing to be limited by theory, it is believed that inhibition of pregenomic RNA encapsidation can ameliorate, abate, or otherwise cause to be controlled, diseases associated with pregenomic RNA encapsidation, for example HBV infection. Pregenomic RNA encapsidation inhibitors of the present invention address the clear and unmet need to identify novel and safe antiviral agents for the treatment of HBV infection that are chemically and mechanistically distinct from HBV antiviral drugs in current clinical use.

Clinically, the pregenomic RNA encapsidation inhibitors of the present invention complement the current medications by providing an additional option for a subpopulation of patients that do not tolerate or benefit from the current medications (Akbar et al., 2009; Liaw, 2009; Peters, 2009; Wiegand, van Bommel, and Berg). In addition, the pregenomic RNA encapsidation inhibitors of the present invention may be effective on HBV variants that are resistant to the currently available DNA polymerase inhibitors (Zoulim and Locarnini, 2009). Further, combination therapies of the pregenomic RNA encapsidation inhibitors of the present invention with DNA polymerase inhibitors may synergistically suppress HBV replication and prevent the emergence of drug resistance, offering a safer and more effective treatment for chronic hepatitis B (Billioud et al., 2011).

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted. "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$ amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $-CF_3$, $-CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocyclyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiophenyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

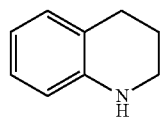

is, for the purposes of the present invention, considered a heterocyclic unit. 6,7-Dihydro-5H-cyclopentapyrimidine having the formula:

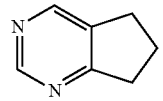

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

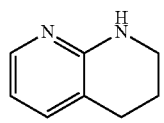

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

For the purposes of the present invention the terms "compound," "analog," and "composition of matter" stand equally well for the pregenomic RNA encapsidation inhibitors described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts: ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Pregenomic RNA Encapsidation Inhibitors

The pregenomic RNA encapsidation inhibitors of the present invention useful for the treatment of Hepatitis B virus (HBV) infection and related conditions are sulfamoyl-benzamide derivatives, and include all enantiomeric and diastereomeric forms and pharmaceutically accepted salts thereof having the formula (I):

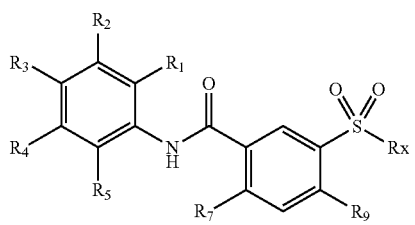

(I)

Including hydrates, solvates, pharmaceutically acceptable salts, pro-drugs and complexes thereof, wherein:
$R^1$ is hydrogen;
$R^2$ is selected from a group consisting of hydrogen, methyl, trifluoromethyl, fluorine, and chlorine;
$R^3$ is selected from a group consisting of hydrogen, methyl, fluorine, and chlorine;
$R^4$ is selected from a group consisting of hydrogen, fluorine, chlorine, and methyl;
$R^5$ is selected from a group consisting of hydrogen and chlorine;
$R^7$ is selected from a group consisting of hydrogen, chlorine, fluorine, and bromine:
$R^9$ is selected from a group consisting of hydrogen, methyl, fluorine, and chlorine;
$R^x$ is selected from a group consisting of $NH_2$,

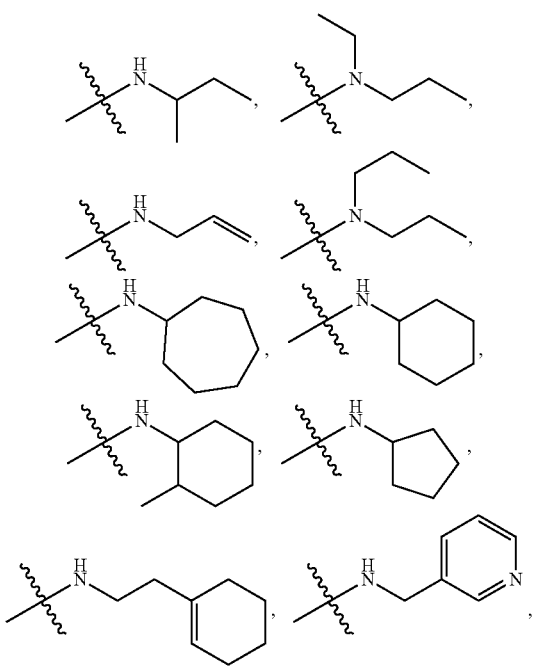

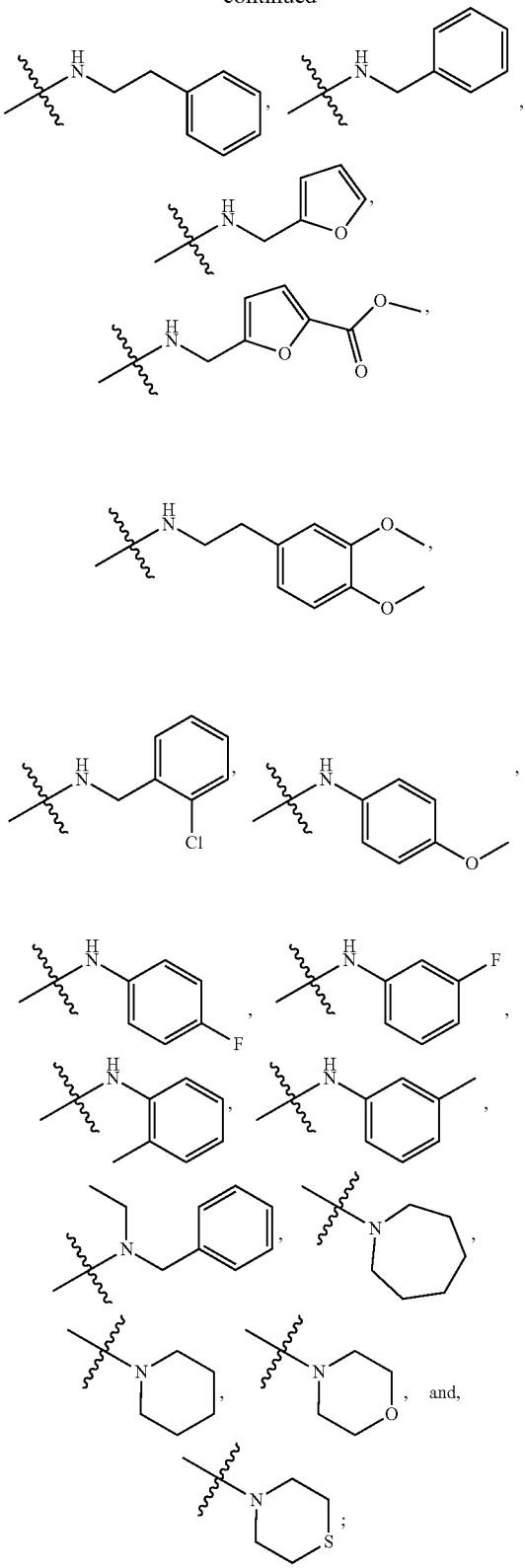

The present invention is further directed toward the novel method of use of sulfamoylbenzamide derivatives of the formula (II), useful as pregenomic RNA encapsidation inhibitors for the treatment of Hepatitis B virus (HBV) infection and related conditions.

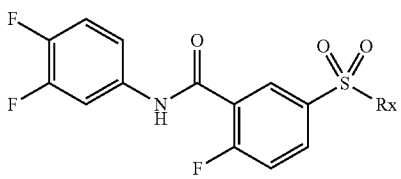
(II)

Including hydrates, solvates, pharmaceutically acceptable salts, prodrugs and complexes thereof, wherein:

$R^x$ is selected from a group consisting of

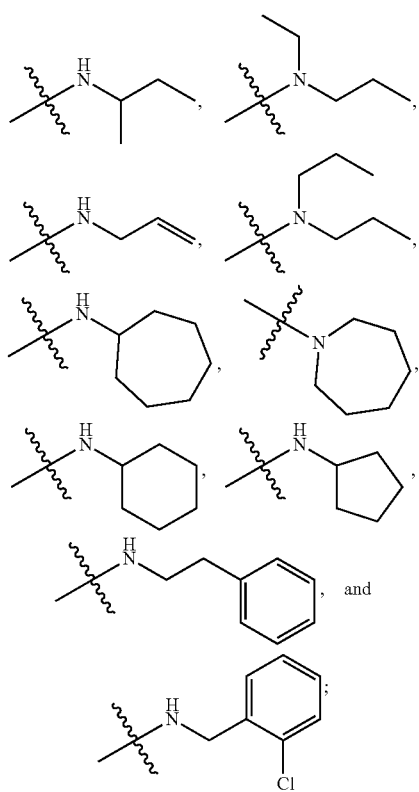

and

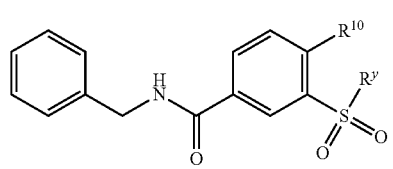

The present invention is further directed toward the novel method of use of sulfamoylbenzamide derivatives of the formula (III), useful as pregenomic RNA encapsidation inhibitors for the treatment of Hepatitis B virus (HBV) infection and related conditions.

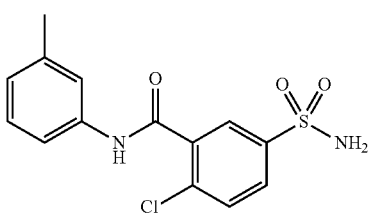 [SMILES: Cc1cccc(NC(=O)c2cc(S(N)(=O)=O)ccc2Cl)c1]
(III)

Including hydrates, solvates, pharmaceutically acceptable salts, pro-drugs and complexes thereof, wherein:

$R^{10}$ is selected from a group consisting of hydrogen, methyl, chlorine, and bromine;

$R^y$ is selected from a group consisting of

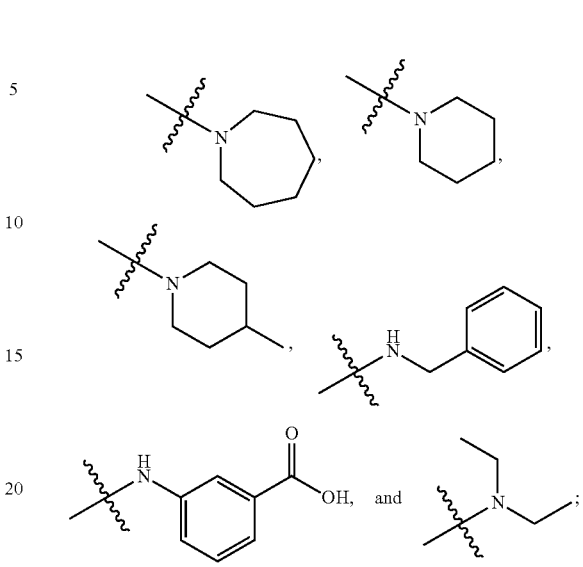

The present invention is further directed toward the novel method of use of sulfamoylbenzamide derivatives of the formula (IV), useful as pregenomic RNA encapsidation inhibitors for the treatment of Hepatitis B virus (HBV) infection and related conditions.

(IV)

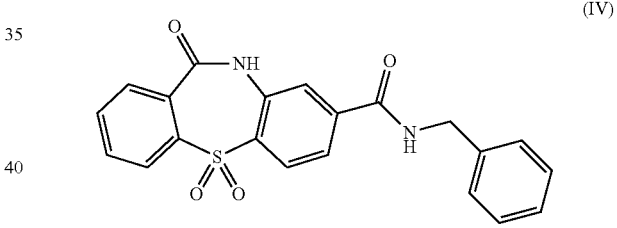

Including hydrates, solvates, pharmaceutically acceptable salts, prodrugs and complexes thereof.

For the purposes of demonstrating the manner in which the compounds of the present invention are named and referred to herein, the compound having the formula:

has the chemical name 2-Chloro-5-sulfamoyl-N-3-methylphenyl-benzamide.

For the purposes of demonstrating the manner in which the compounds of the present invention are named and referred to herein, the compound having the formula:

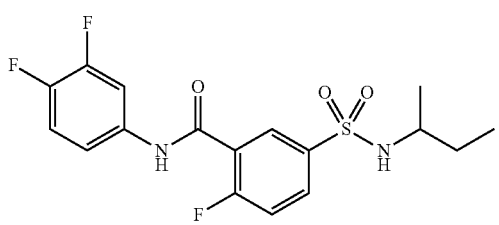

has the chemical name 5-(2-Butylsulfamoyl)-N-(3,4-difluoro-phenyl)-2-fluoro-benzamide.

For the purposes of demonstrating the manner in which the compounds of the present invention are named and referred to herein, the compound having the formula:

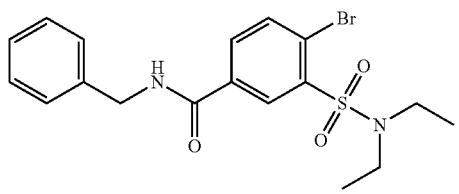 [SMILES: CCN(CC)S(=O)(=O)c1cc(C(=O)NCc2ccccc2)ccc1Br]

has the chemical name N-Benzyl-4-bromo-3-diethylsulfamoyl-benzamide.

For the purposes of demonstrating the manner in which the compounds of the present invention are named and referred to herein, the compound having the formula:

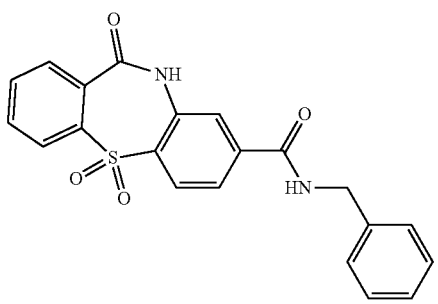 [SMILES: O=C(NCc1ccccc1)c1ccc2c(c1)NC(=O)c1ccccc1S2(=O)=O]

has the chemical name 5,5,11-Trioxo-10,11-dihydro-5H-516-dibenzo[b,f][1,4]thiazepine-8-carboxylic acid benzylamide.

For the purposes of the present invention, a compound depicted by the racemic formula, for example:

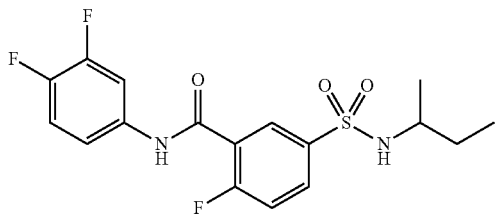 [SMILES: CCC(C)NS(=O)(=O)c1ccc(F)c(C(=O)Nc2ccc(F)c(F)c2)c1]

will stand equally well for either of the two enantiomers having the formula:

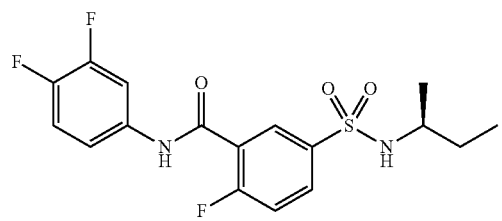 [SMILES: CC[C@H](C)NS(=O)(=O)c1ccc(F)c(C(=O)Nc2ccc(F)c(F)c2)c1]

or the formula:

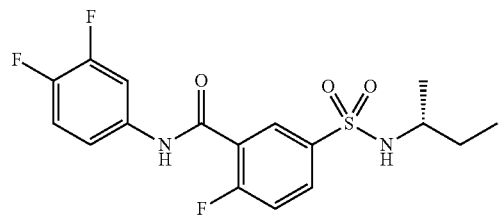 [SMILES: CC[C@@H](C)NS(=O)(=O)c1ccc(F)c(C(=O)Nc2ccc(F)c(F)c2)c1]

or mixtures thereof, or in the case where a second chiral center is present, all diastereomers.

In some embodiments, $R^1$ is hydrogen.
In some embodiments, $R^2$ is hydrogen.
In some embodiments, $R^2$ is methyl.
In some embodiments, $R^2$ is trifluoromethyl.
In some embodiments, $R^2$ is fluorine.
In some embodiments, $R^2$ is chlorine.
In some embodiments, $R^3$ is hydrogen.
In some embodiments, $R^3$ is methyl.
In some embodiments, $R^3$ is fluorine.
In some embodiments, $R^3$ is chlorine.
In some embodiments, $R^4$ is hydrogen.
In some embodiments, $R^4$ is methyl.
In some embodiments, $R^4$ is fluorine.
In some embodiments, $R^4$ is chlorine.
In some embodiments, $R^5$ is hydrogen.
In some embodiments, $R^5$ is chlorine.
In some embodiments, $R^7$ is hydrogen.
In some embodiments, $R^7$ is chlorine.
In some embodiments, $R^7$ is fluorine.
In some embodiments, $R^7$ is bromine.
In some embodiments, $R^9$ is hydrogen.
In some embodiments, $R^9$ is methyl.
In some embodiments, $R^9$ is fluorine.
In some embodiments, $R^9$ is chlorine.
In some embodiments, $R^x$ is $NH_2$.
In some embodiments, $R^x$ is

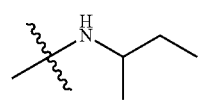 [SMILES: *NC(C)CC]

In some embodiments, $R^x$ is

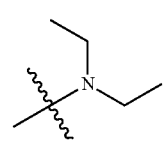 [SMILES: *N(CC)CC]

In some embodiments, $R^x$ is

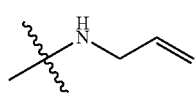

In some embodiments, $R^x$ is

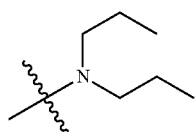 [SMILES: *N(CCC)CCC]

In some embodiments, $R^x$ is

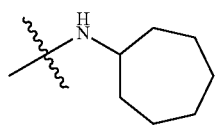 [SMILES: *NC1CCCCCC1]

In some embodiments, $R^x$ is

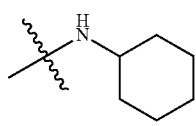

In some embodiments, $R^x$ is

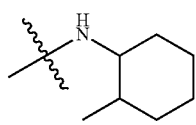 [SMILES: *NC1CCCCC1C]

In some embodiments, $R^x$ is

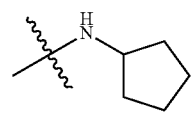 [SMILES: *NC1CCCC1]

In some embodiments, $R^x$ is

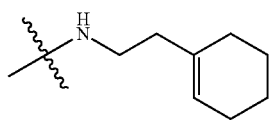 [SMILES: *NCCC1=CCCCC1]

In some embodiments, $R^x$ is

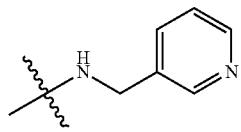 [SMILES: *NCc1cccnc1]

In some embodiments, $R^x$ is

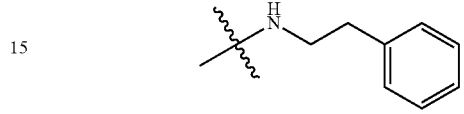

In some embodiments, $R^x$ is

In some embodiments, $R^x$ is

In some embodiments, $R^x$ is

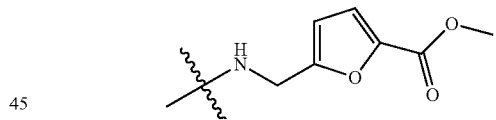

In some embodiments, $R^x$ is

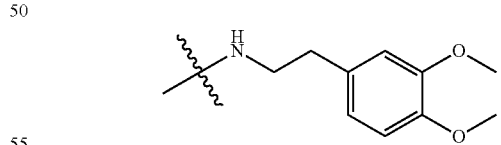

In some embodiments, $R^x$ is

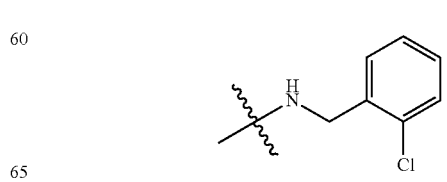

In some embodiments, $R^x$ is

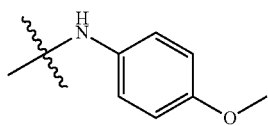 [SMILES: *Nc1ccc(OC)cc1]

In some embodiments, $R^x$ is

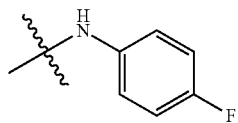 [SMILES: *Nc1ccc(F)cc1]

In some embodiments, $R^x$ is

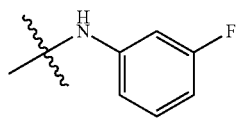 [SMILES: *Nc1cccc(F)c1]

In some embodiments, $R^x$ is

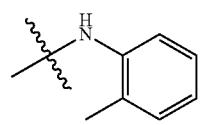 [SMILES: *Nc1ccccc1C]

In some embodiments, $R^x$ is

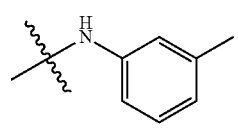 [SMILES: *Nc1cccc(C)c1]

In some embodiments, $R^x$ is

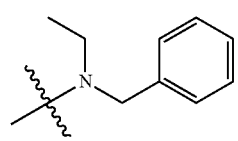 [SMILES: *N(CC)Cc1ccccc1]

In some embodiments, $R^x$ is

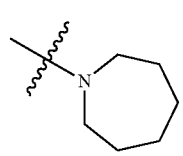 [SMILES: *N1CCCCCC1]

In some embodiments, $R^x$ is

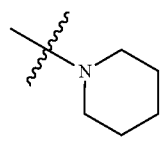 [SMILES: *N1CCCCC1]

In some embodiments, $R^x$ is

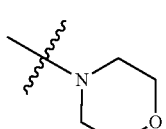

In some embodiments, $R^x$ is

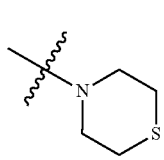

In some embodiments, $R^{10}$ is hydrogen.
In some embodiments, $R^{10}$ is methyl.
In some embodiments, $R^{10}$ is chlorine.
In some embodiments, $R^{10}$ is bromine.
In some embodiments, $R^y$ is

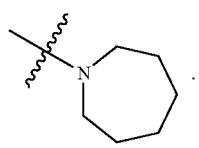

In some embodiments, $R^y$ is

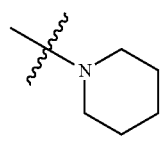 [SMILES: *N1CCCCC1]

In some embodiments, $R^y$ is

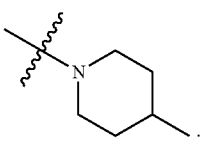 [SMILES: *N1CCC(C)CC1]

In some embodiments, $R^y$ is

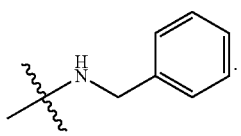

In some embodiments, $R^y$ is

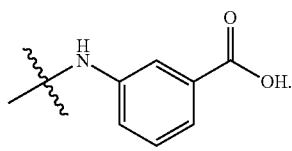 [SMILES: *Nc1cccc(C(=O)O)c1]

In some embodiments, $R^y$ is

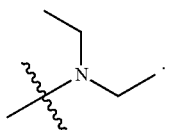 [SMILES: *N(CC)CC]

Exemplary embodiments include compounds having the formula (V) or a pharmaceutically acceptable salt form thereof:

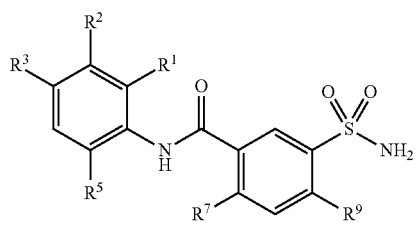

(V)

wherein non-limiting examples of $R^1$, $R^2$, $R^3$, $R^5$, $R^7$ and $R^9$ are defined herein below in Table 1.

TABLE 1

Exemplary embodiments of compounds of the formula (V):

| Compound Name | $R_1$ | $R_2$ | $R_3$ | $R_5$ | $R_7$ | $R_9$ |
|---|---|---|---|---|---|---|
| DVR-16 | H | CH$_3$ | H | H | Cl | H |
| DVR-19 | H | CF$_3$ | H | H | H | F |
| DVR-21 | H | CF$_3$ | H | Cl | H | F |
| DVR-22 | H | H | H | H | H | H |

Exemplary embodiments include compounds having the formula (VI) or a pharmaceutically acceptable salt form thereof:

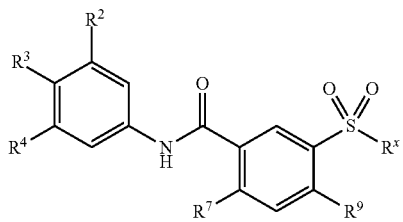

(VI)

wherein non-limiting examples of $R^2$, $R^3$, $R^4$, $R^7$, $R^9$, and $R^x$ are defined herein below in Table 2.

TABLE 2

Exemplary embodiments of compounds of the formula (VI):

| Compound | $R^2$ | $R^3$ | $R^4$ | $R^7$ | $R^9$ | $R^x$ |
|---|---|---|---|---|---|---|
| DVR-23 | F | F | H | F | H | 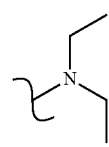 |
| DVR-24 | H | H | H | H | H | 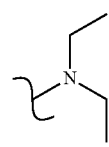 |
| DVR-25 | F | F | H | F | H | 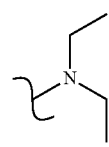 |

TABLE 2-continued

Exemplary embodiments of compounds of the formula (VI):

| Compound | R² | R³ | R⁴ | R⁷ | R⁹ | Rˣ |
|---|---|---|---|---|---|---|
| DVR-26 | CH₃ | H | H | Cl | H | −N(CH₂CH₃)₂ |
| DVR-27 | H | Cl | H | H | H | −N(CH₂CH₃)₂ |
| DVR-34 | F | F | H | F | H | −NH−CH₂−CH=CH₂ |
| DVR-42 | F | F | H | F | H | −N(CH₂CH₂CH₃)₂ |
| DVR-43 | F | F | H | F | H | −NH−cycloheptyl |
| DVR-44 | H | CH₃ | H | F | H | −NH−cycloheptyl |
| DVR-45 | F | F | H | F | H | −NH−cyclohexyl |
| DVR-47 | H | H | H | Br | H | −NH−cyclohexyl |
| DVR-51 | H | F | H | H | Cl | −NH−cyclohexyl |
| DVR-52 | H | H | H | H | CH₃ | −NH−cyclohexyl |
| DVR-53 | F | F | H | H | F | −NH−(2-methylcyclohexyl) |

TABLE 2-continued

Exemplary embodiments of compounds of the formula (VI):

| Compound | $R^2$ | $R^3$ | $R^4$ | $R^7$ | $R^9$ | $R^X$ |
|---|---|---|---|---|---|---|
| DVR-55 | H | H | H | H | H | -NH-cyclopentyl |
| DVR-56 | F | F | H | F | H | -NH-cyclopentyl |
| DVR-57 | H | F | H | F | H | -NH-cyclopentyl |
| DVR-61 | CH$_3$ | H | CH$_3$ | F | H | -NH-cyclopentyl |
| DVR-62 | CH$_3$ | H | H | H | F | -NH-cyclopentyl |
| DVR-63 | Cl | H | Cl | F | H | -NH-cyclopentyl |
| DVR-64 | H | H | H | H | H | -NH-CH$_2$-furan-2-yl |
| DVR-65 | Cl | F | H | F | H | -NH-CH$_2$-furan-2-yl |
| DVR-66 | F | H | H | F | H | -NH-CH$_2$-furan-2-yl |
| DVR-68 | Cl | H | Cl | F | H | -NH-CH$_2$-furan-2-yl |
| DVR-69 | CH$_3$ | H | H | H | F | -NH-CH$_2$-furan-2-yl |
| DVR-70 | H | H | H | Cl | H | -NH-CH$_2$-(5-methoxycarbonyl-furan-2-yl) |

TABLE 2-continued
Exemplary embodiments of compounds of the formula (VI):
| Compound | R² | R³ | R⁴ | R⁷ | R⁹ | Rˣ |
|---|---|---|---|---|---|---|
| DVR-73 | Cl | H | H | F | H | 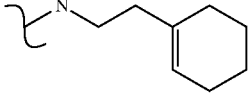 |
| DVR-74 | CH₃ | H | CH₃ | F | H | 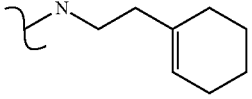 |
| DVR-75 | H | H | H | H | H | 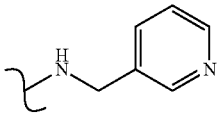 |
| DVR-77 | Cl | H | H | H | F | 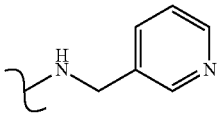 |
| DVR-82 | F | F | H | F | H | 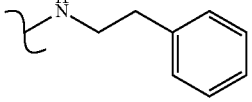 |
| DVR-83 | Cl | H | H | F | H | 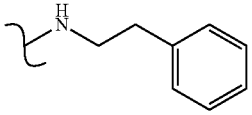 |
| DVR-87 | Cl | F | H | F | H | 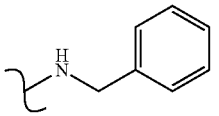 |
| DVR-89 | H | H | H | Cl | H | 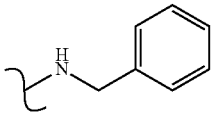 |
| DVR-91 | H | Cl | H | F | H | 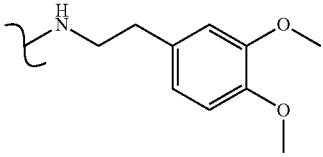 |
| DVR-92 | F | F | H | F | H | 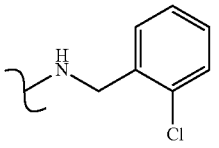 |
| DVR-93 | H | Cl | H | H | F | 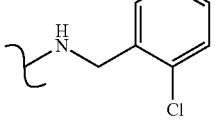 |

TABLE 2-continued

Exemplary embodiments of compounds of the formula (VI):

| Compound | R² | R³ | R⁴ | R⁷ | R⁹ | Rˣ |
|---|---|---|---|---|---|---|
| DVR-94 | CH₃ | H | H | F | H | -NH-C₆H₄-OCH₃ (4-methoxyanilino) |
| DVR-96 | CH₃ | H | H | F | H | -NH-C₆H₄-F (4-fluoroanilino) |
| DVR-98 | H | Cl | H | H | H | -NH-C₆H₄-F (3-fluoroanilino) |
| DVR-100 | H | Cl | H | H | H | -NH-C₆H₄-CH₃ (2-methylanilino) |
| DVR-101 | H | H | H | H | H | -NH-C₆H₄-CH₃ (3-methylanilino) |
| DVR-102 | H | H | H | H | H | -NH-C₆H₄-CH₃ (2-methylanilino) |
| DVR-103 | F | F | H | H | F | N(Et)(CH₂Ph) |
| DVR-104 | F | F | H | F | H | azepan-1-yl |
| DVR-107 | H | H | H | H | CH₃ | piperidin-1-yl |
| DVR-108 | H | F | H | H | Cl | piperidin-1-yl |
| DVR-115 | F | H | H | H | Cl | morpholin-4-yl |

TABLE 2-continued

Exemplary embodiments of compounds of the formula (VI):

| Compound | R² | R³ | R⁴ | R⁷ | R⁹ | Rˣ |
|---|---|---|---|---|---|---|
| DVR-117 | H | H | H | H | Cl | (thiomorpholinylmethyl) |

Exemplary embodiments include compounds having the formula (II) or a pharmaceutically acceptable salt form thereof:

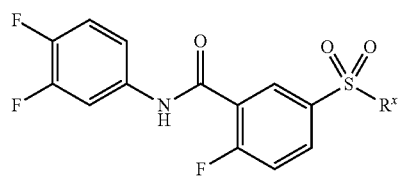

(II)

wherein non-limiting examples of Rˣ are defined herein below in Table 3.

TABLE 3

Exemplary embodiments of compounds of the formula (II):

| Compound | Rˣ |
|---|---|
| DVR-23 | NH-propyl |
| DVR-25 | N(ethyl)₂ |
| DVR-34 | NH-allyl |
| DVR-42 | N(propyl)₂ |
| DVR-43 | NH-cycloheptyl |
| DVR-104 | azepanyl |

TABLE 3-continued

Exemplary embodiments of compounds of the formula (II):

| Compound | Rˣ |
|---|---|
| DVR-45 | NH-cyclohexyl |
| DVR-56 | NH-cyclopentyl |
| DVR-82 | NH-CH₂CH₂-phenyl |
| DVR-92 | NH-CH₂-(2-chlorophenyl) |

Exemplary embodiments include compounds having the formula (III) or a pharmaceutically acceptable salt form thereof:

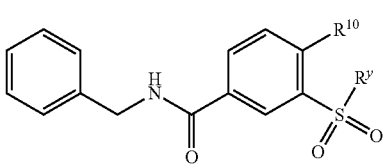

(III)

wherein non-limiting examples of Rʸ are defined herein below in Table 3.

TABLE 4

Exemplary embodiments of compounds of the formula (III):

| Compound | R¹⁰ | Rʸ |
|---|---|---|
| DVR-01 | Cl | azepanyl |

TABLE 4-continued

Exemplary embodiments of compounds of the formula (III):

| Compound | R[10] | R[y] |
|---|---|---|
| DVR-02 | Cl | piperidinyl |
| DVR-08 | CH₃ | 4-methylpiperidinyl |
| DVR-09 | CH₃ | -NH-CH₂-phenyl |
| DVR-10 | H | -NH-(3-carboxyphenyl) |
| DVR-11 | Br | -N(CH₂CH₃)₂ |

Exemplary embodiments include a compound having the formula (IV) or a pharmaceutically acceptable salt form thereof:

(IV)

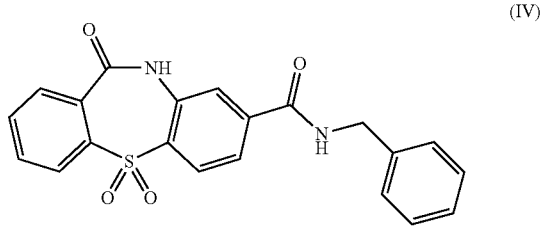 [SMILES: O=C(NCc1ccccc1)c1ccc2c(c1)NC(=O)c1ccccc1S2(=O)=O]

In all of the embodiments provided herein, examples of suitable optional substituents are not intended to limit the scope of the claimed invention. The compounds of the invention may contain any of the substituents, or combinations of substituents, provided herein.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature.

EXAMPLES

The examples below provide methods for preparing representative compounds of formula (II). The skilled practitioner will know how to substitute the appropriate reagents, starting materials and purification methods known to those skilled in the art, in order to prepare additional compounds of the present invention.

Example 1: Synthesis of 5-cyclopentylsulfamoyl-N-(3,4-difluoro-phenyl)-2-fluoro-benzamide (DVR-56)

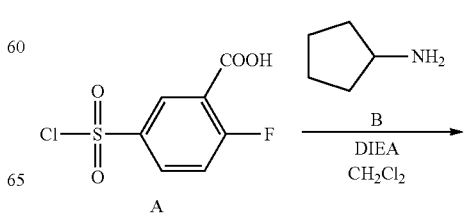

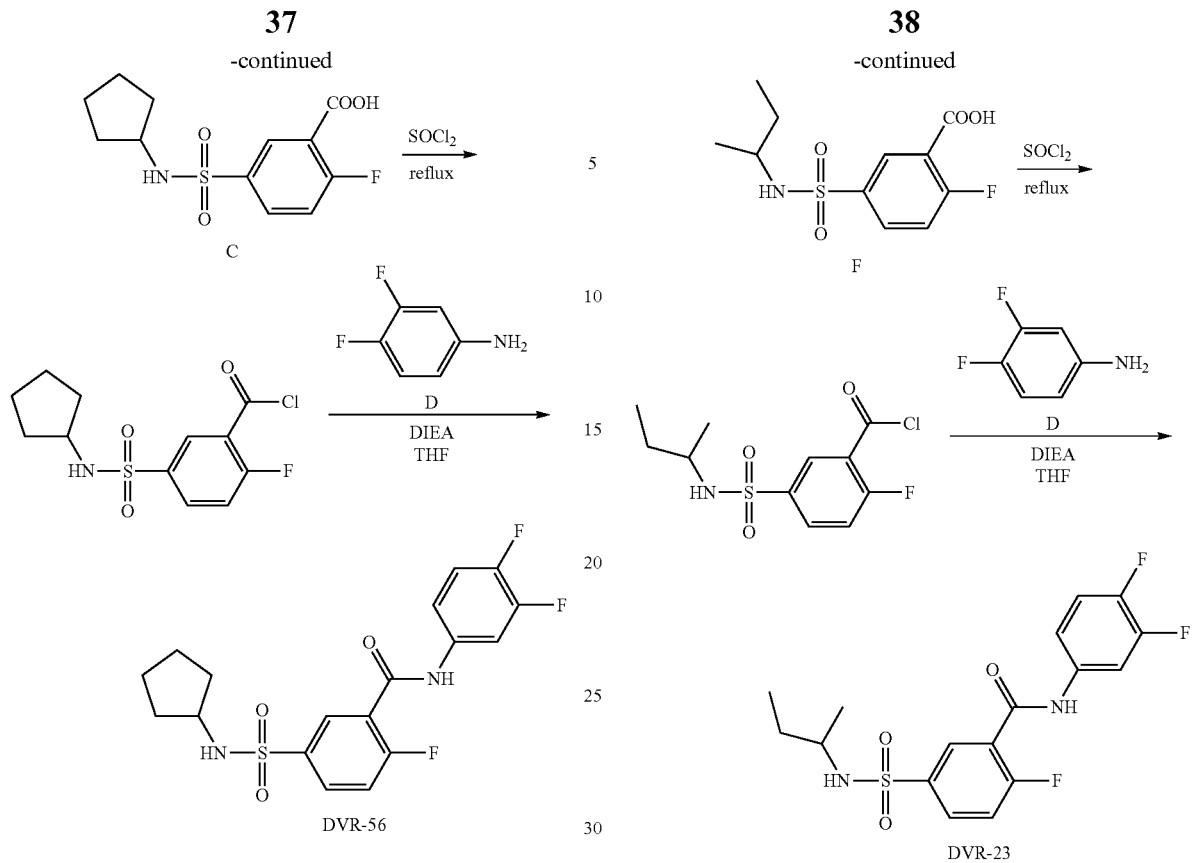

5-Chlorosulfonyl-2-fluoro-benzoic acid (A, 0.506 g, 0.0021 mol), cyclopentylamine (B, 0.1806 g, 0.00212 mol) and diisopropylethyl amine (DIEA, 1.1 mL, 0.00636 mol) in CH$_2$Cl$_2$ were stirred at room temperature overnight. The solvent was evaporated and the crude product was purified by silica gel chromatography (MeOH containing 10% AcOH)/CH$_2$Cl$_2$) to give 5-cyclopentylsulfamoyl-2-fluoro-benzoic acid (C, 0.55 g, 90%). After drying overnight under vacuum, C (0.48 g, 0.0016 mol) in SOCl$_2$ (5 mL) was heated at 80° C. for 3 hours, after which the SOCl$_2$ was evaporated and the residue was dried overnight. The residue was then dissolved in tetrahydrofuran (5 mL), 3,4-Difluoro-phenylamine (D, 0.216 g, 0.00167 mol) was added followed by diisopropylethyl amine (0.5 mL). The mixture was heated to 70° C. overnight. The solvent was evaporated, followed by ethyl acetate extraction. After purification by silica gel chromatography (ethyl acetate/hexane), 0.3 g (45%) of 5-cyclopentylsulfamoyl-N-(3,4-difluoro-phenyl)-2-fluoro-benzamide (DVR-56) was obtained.

5-Chlorosulfonyl-2-fluoro-benzoic acid (A, 0.506 g, 0.0021 mol), sec-butylamine (E, 0.155 g, 0.00212 mol) and DIEA (1.1 mL, 0.00636 mol) in CH$_2$Cl$_2$ were stirred at room temperature overnight. The solvent was evaporated and the crude product was purified by silica gel chromatography (MeOH containing 10% AcOH/CH$_2$Cl$_2$) to give 5-sec-Butylsulfamoyl-2-fluoro-benzoic acid (F, 0.56 g, 96%). After drying overnight under vacuum, F (0.56 g, 0.0020 mol) in SOCl$_2$ (5 mL) was heated at 80° C. for 3 hours, after which the SOCl$_2$ was evaporated and the residue was dried overnight. The residue was then dissolved in tetrahydrofuran (5 mL), 3,4-difluoro-phenylamine (D, 0.26 g, 0.0020 mol) was added followed by DIEA (0.8 mL). The mixture was heated to 70° C. overnight. The solvent was evaporated, followed by ethyl acetate extraction. After purification by silica gel chromatography (ethyl acetate/hexane), 0.45 g (57%) of 5-sec-butylsulfamoyl-N-(3,4-difluoro-phenyl)-2-fluoro-benzamide (DVR-23) was obtained.

Example 2: Synthesis of 5-sec-butylsulfamoyl-N-(3,4-difluoro-phenyl)-2-fluoro-benzamide (DVR-23)

Example 3: Synthesis of 5-cyclohexylsulfamoyl-N-(3,4-difluoro-phenyl)-2-fluoro-benzamide (DVR-45)

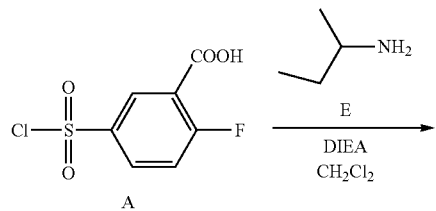

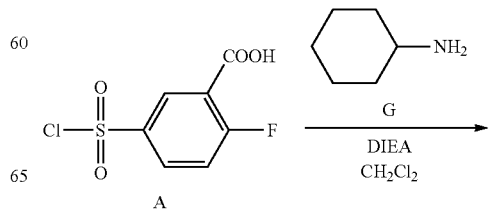

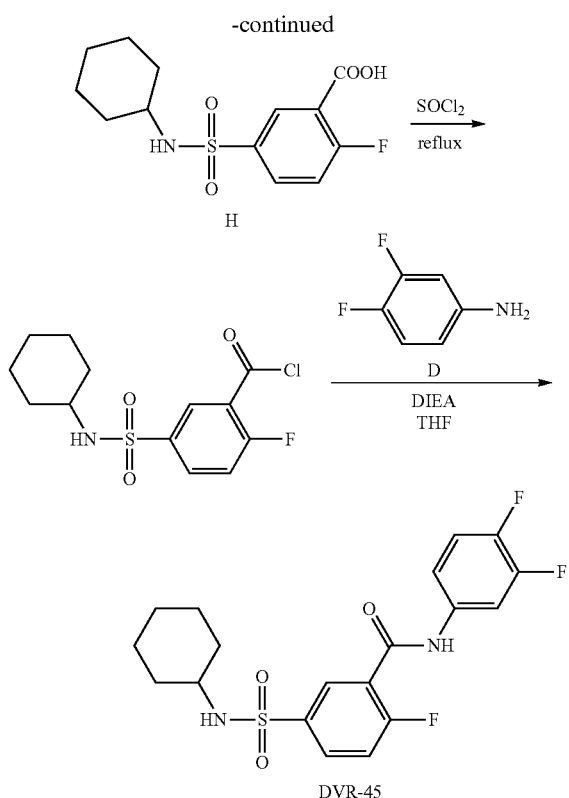

DVR-45

5-Chlorosulfonyl-2-fluoro-benzoic acid (A, 0.508 g, 0.0021 mol), Cyclohexylamine (G, 0.211 g, 0.00212 mol) and DIEA (1.1 mL, 0.00636 mol) in $CH_2Cl_2$ were stirred at room temperature overnight. The solvent was evaporated and the crude product was purified by silica gel chromatography (MeOH containing 10% AcOH/$CH_2Cl_2$) to give 5-cyclohexylsulfamoyl-2-fluoro-benzoic acid (H, 0.6 g, 95%). After drying overnight under vacuum, H (0.22 g, 0.737 mmol) in $SOCl_2$ (5 mL) was heated at 80° C. for 2 hours after which the $SOCl_2$ was evaporated and the residue was dried overnight. The residue was then dissolved in tetrahydrofuran (5 mL), 3,4-difluoro-phenylamine (D, 95 mg, 0.737 mmol) was added followed by DIEA (0.8 mL). The mixture was heated to 70° C. overnight. The solvent was evaporated, followed by ethyl acetate extraction. After purification by silica gel chromatography (ethyl acetate/hexane), 0.192 g (63%) of 5-cyclohexylsulfamoyl-N-(3,4-difluoro-phenyl)-2-fluoro-benzamide (DVR-45) was obtained.

Formulations

The present invention also relates to compositions or formulations which comprise the pregenomic RNA encapsidation inhibitors according to the present invention. In general, the compositions of the present invention comprise an effective amount of one or more sulfamoylbenzamide derivatives and salts thereof according to the present invention which are effective for useful for the treatment of Hepatitis H virus (HBV) infection and related conditions; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known antiviral agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more pregenomic RNA encapsidation inhibitors according to the present invention and one or more excipients; from about 0.01 mg to about 100 mg of one or more pregenomic RNA encapsidation inhibitors according to the present invention and one or more excipients; and from about 0.1 mg to about 10 mg of one or more pregenomic RNA encapsidation inhibitors according to the present invention; and one or more excipients.

Procedures

The following procedures can be utilized in evaluating and selecting compounds as the pregenomic RNA encapsidation inhibitors of HBV.

The HBV replication inhibitors of the present invention are capable of treating and preventing diseases associated with HBV infection. The results presented in Tables 5 to 9 demonstrated that compounds of the present invention inhibit HBV replication in an immortalized murine hepatocyte (AML12)-derived stable cell line (AML12HBV10) that supports robust HBV replication in a tetracycline inducible manner without measurable cytotoxicity up to 50 µM by using the standard MTT assay (Promega).

The antiviral efficacy of the compounds of the disclosure, as presented in Tables 5, 6, 7, 8 and 9, were determined in AML12HBV10 cells. AML12HBV10 is an immortalized murine hepatocyte (AML12)-derived stable cell line that supports robust HBV replication in a tetracycline inducible manner (Xu et al.). The cells were seeded into 96 well plates at a density of $2 \times 10^4$ cells per well and cultured in DMEM/F12 media with 10% fetal bovine serum in the absence of tetracycline to allow pgRNA transcription and HBV DNA replication. One day after seeding, cells were left untreated or treated with a serial dilution of testing compounds, ranging from 50 µM to 0.39 µM, for 48 hours. Cells were then lysed by adding into each well of 100 µl lysis buffer containing 10 mM Tris-HCl (pH 7.6), 1 mM EDTA, 100 mM NaCl and 1% NP-40 and incubated at 37° C. for 30 minutes. Half amount (50 µl) of cell lysate from each well was combined with equal volume of denaturing solution containing 0.5N NaOH and 1.5M NaCl. After 5 minute incubation, 100 µl of neutralization solution (1M Tris-HCl, pH 7.4, 1.5M NaCl) was added into each well. The denatured cell lysates (totally 200 µl) were applied onto Nylon membrane using 96-well dot-blot manifold (Biorad). HBV DNA in the cell lysates were determined by dot-blot hybridization with alpha-$^{32}$P-UTP-labelled riboprobe specific for HBV minus strand DNA. The antiviral efficacy of a compound of the disclosure was expressed as the concentration that reduces the amount of HBV DNA by 50% ($EC_{50}$).

Determination of cytotoxicity of compounds of the disclosure in AML12HBV10 cells: To determine the cytotoxicity of the compounds, AML12HBV10 cells were seeded into 96-well plates at a density of $2 \times 10^4$ cells per well and cultured in DMEM/F12 media with 10% fetal bovine serum in the absence of tetracycline to allow pgRNA transcription and HBV DNA replication. One day after seeding, cells were left untreated or treated with a serial dilution of testing compounds, ranging from 50 µM to 0.39 µM, for 48 hours. The cell viability was measured by a MTT assay, following procedure provided by the manufacturer (Promega). The cytotoxicity of a compound was expressed as the concentration of compound that reduces the viability of the cells by 50% ($CC_{50}$).

Figure 2:
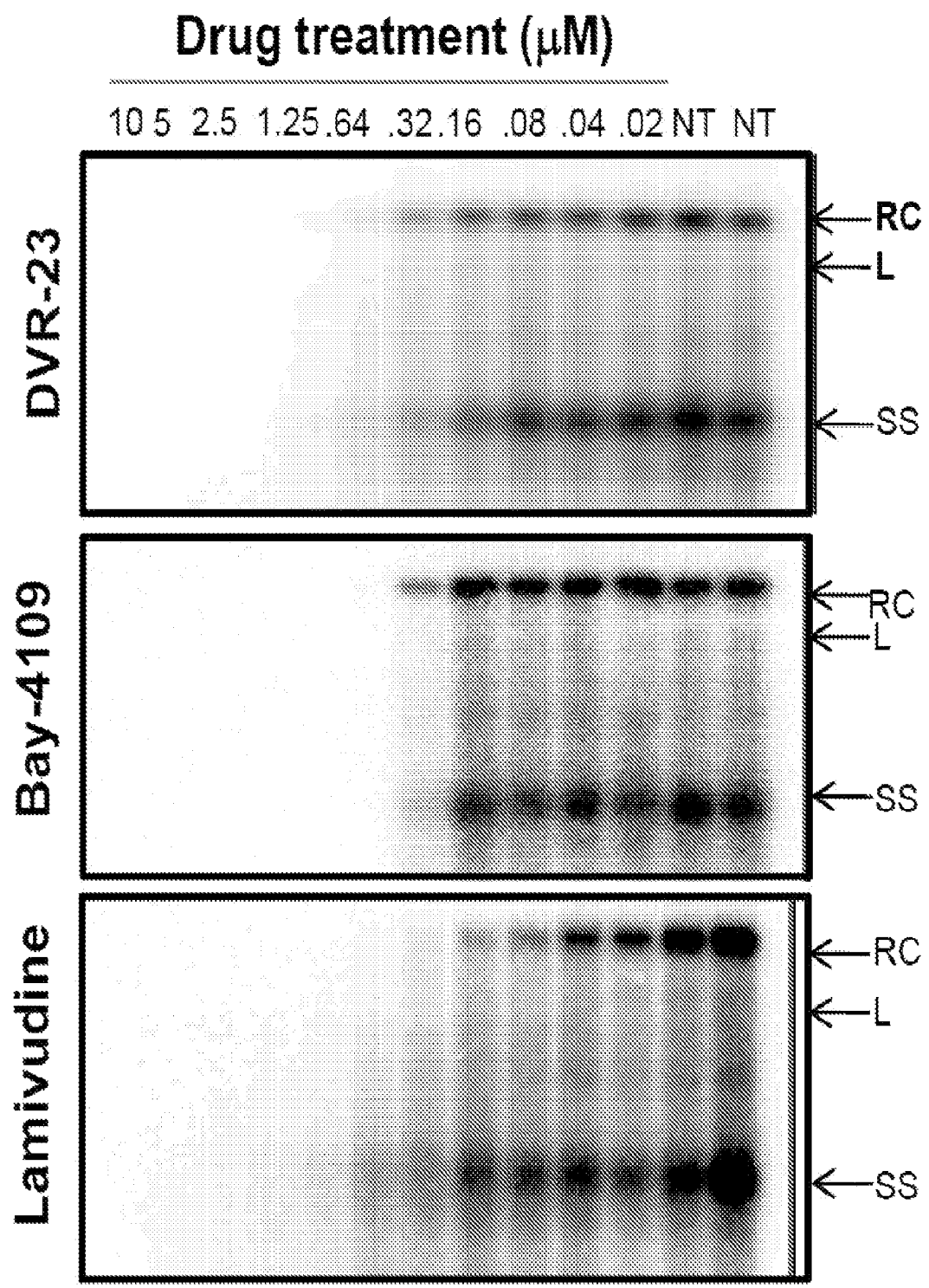
FIG. 2: Comparison of antiviral activity of DVR-23 with Lamivudine and Bay 41-4109. HepDES19 cells were left untreated (NT) or treated with the indicated concentrations (μM) of DVR-23, Lamivudine or Bay 41-4109 for 4 days. Cytoplasmic core-associated HBV DNA replication intermediates were extracted and determined by Southern blot hybridizations. RC, L and SS indicate relaxed circular, double-stranded linear and single-stranded HBV DNA, respectively.

Determination of antiviral activity of compounds of the disclosure, as presented in FIG. 1. FIG. 2 and Table 10, in human hepatoma-derived cell lines: To further confirm the antiviral activity of the compounds of the disclosure against HBV in human hepatocyte-derived cells, HepDES19 cells, a human hepatoma cell line supporting HBV replication in a tetracycline inducible manner (Guo et al., 2007), seeded into 12-well plates at a density of $5 \times 10^5$ cells per well and cultured in DMEM/F12 media with 10% fetal bovine serum and 1 µg/ml tetracycline. Two days after seeding, the cells were mock-treated or treated with a serial dilution of compounds of the disclosure, ranging from 10 µM to 0.018 µM, for 6 days in the absence of tetracycline. Upon the completion of treatment, cells were lysed by adding into each well of the 12-well plates 0.5 ml of lysis buffer containing 10 mM Tris-HCl (pH 8.0), 1 mM EDTA, 1% NP40 and 2% sucrose and incubating at 37° C. for 10 minutes. Cell debris and nuclei were removed by centrifugation and the supernatant was mixed with 130 µl of 35% polyethylene glycol (PEG) 8000 containing 1.5 M NaCl. After 1 hour incubation in ice, viral nucleocapsids were pelleted by centrifugation at 6,000×g for 5 min at 4° C., followed by 1 hour digestion at 37° C. in 400 µl of digestion buffer containing 0.5 mg/ml pronase (Calbiochem), 0.5% SDS, 150 mM NaCl, 25 mM Tris-HCl (pH 8.0) and 10 mM EDTA. The digestion mixture was extracted twice with phenol and DNA was precipitated with ethanol, dissolved in TE buffer (10 mM Tris-HCl, pH 8.0; 0.1 mM EDTA). One half of the DNA sample from each well was resolved by electrophoresis into a 1.5% agarose gel. The gel was then subjected to denaturation in a solution containing 0.5 M NaOH and 1.5 M NaCl, followed by neutralization in a buffer containing 1 M Tris-HCl (pH7.4) and 1.5 M NaCl. DNA was then blotted onto Hybond-XL membrane (GE Health care) in 20×SSC buffer. The amounts of cytoplasmic HBV core-associated HBV DNA were determined by Southern blot hybridization and the antiviral efficacy of a compound was expressed as its concentration that reduce the amount of HBV DNA by 50% ($EC_{50}$) or 90% ($EC_{90}$).

Determination of cytotoxicity of compounds of the disclosure in human hepatoma-derived cell lines, HepDES19 cells were seeded into 96-well plates at a density of 6×10 cells per well and cultured in DMEM/F12 media with 10% fetal bovine serum in the absence of tetracycline. One day after seeding, cells were left untreated or treated with a serial dilution of testing compounds, ranging from 50 µM to 0.39 µM, for 6 days. The cell viability was measured by a MTT assay, following procedure provided by the manufacturer (Promega). The cytotoxicity of a compound was expressed as the concentration of compound that reduces the viability of the cells by 50% ($CC_{50}$).

Antiviral efficacy of the selective compounds of the disclosure in HepDES19 cells is presented in FIG. 1. A side-by-side comparison of the antiviral efficacy between DVR23 and two known anti-HBV compounds, lamivudine and Bay 41-4109 is presented in FIG. 2. A summary of the antiviral efficacy and cytotoxicity of representative compounds of the disclosure in AML12HBV10 and HepDES19 cells is presented in Table 10. These results clearly demonstrate that the compounds of the disclosure selectively inhibit HBV replication not only in murine hepatocyte-derived cell line (AML12HBV10), but also in human hepatocyte-derived cell line (HepDES19). The results also demonstrate that DVR-26 inhibits HBV DNA replication at a similar efficacy of lamivudine and Bay 41-4109.

To obtain mechanistic insight of the compounds of present invention against HBV, AML12HBV10 cells cultured in the 12-well plates were treated with a series of concentrations of DVR-1, DVR-56 or DVR-23 for two days in the absence of tetracycline (Guo et al., 2007). As positive controls, the cells were also treated with Bay41-4109 (5 µM) or AT-61 (25 µM), the known HBV nucleocapsid assembly effectors that either bind to HBV core protein dimmer to misdirect its interaction and prevent capsid formation (Bay41-4109) (Deres et al., 2003: Stray and Zlotnick, 2006), or interact with a core assembly intermediate and promote the formation of empty capsids (AT-61) (Feld et al., 2007; Katen et al., King et al., 1998). The amounts of intracellular viral mRNA, encapsidated pgRNA, capsids and nucleocapsid-associated HBV DNA were analyzed with the methods detailed below.

Procedure for analysis of HBV mRNA: Upon the completion of treatment, total cellular RNA was extracted with TRIzol reagents (Invitrogen). Five micrograms of total RNA was resolved in 1.5% agarose gel containing 2.2 M formaldehyde and transferred onto Hybond-XL membrane in 20×SSC buffer. The amounts of HBV mRNA were determined by Northern blot hybridization with an alpha-$^{32}$P-UTP labeled riboprobe specific for plus strand of HBV genome.

Determination of encapsidated pgRNA: AML12HBV10 cells were lysed by addition of 600 µl of lysis buffer (50 mM Tris-HCl [pH 7.5], 1 mM EDTA, 150 mM NaCl, 1% NP-40) into each well of 12-well plates. The nuclei were removed by centrifugation at 5,000 g for 10 minutes. One-half of the sample was mixed with 6 U of micrococcal nuclease (Pharmacia) and 15 µl of 100 mM $CaCl_2$ and incubated for 15 minutes at 37° C. to digest free nucleic acids. The reaction was stopped with 6 µl of 0.5 M EDTA, and capsids were precipitated by adding 125 µl of 35% polyethylene glycol 8000 in 1.75 M NaCl to the reaction and incubating in ice for 30 minutes, followed by centrifugation at 6,000 g for 10 minutes at 4° C. Pellets were re-suspended in 50 µl of TNE buffer (10 mM Tris-HCl [pH 8], 100 mM NaCl, 1 mM EDTA), pgRNA was extracted by the addition of 1 ml of Trizol reagent. The encapsidated pgRNA were electrophoresed through a 2.2 M formaldehyde-1% agarose gel, transferred to a nylon membrane, and immobilized by UV cross-linking (Stratagene). Hybridization was performed with an alpha-$^{32}$P-UTP labeled riboprobe specific for plus strand of HBV genome.

Procedures of viral capsids and nucleocapsid-associated DNA analysis: HepDES19 cells were lysed by addition of 300 µl buffer containing 10 mM Tris-HCl (pH7.6), 100 mM NaCl, 1 mM EDTA and 0.1% NP-40 to each well of 12-well plate. Cell debries were removed by centrifugation at 5000 g for 10 minutes. Ten microliters of the clarified cell lysates were fractionated by electrophoresis through nondenaturing 1% agarose gels and transferred to a nitrocellulose filter by blotting with TNE buffer (10 mM Tris-HCl, pH17.6; 150 mM NaCl and 1 mM EDTA). HBV capsids were detected by probing the membrane with an antibody against HBV core protein (DAKO). Bound antibody was revealed by IRDye secondary antibobies and visualized by Li-COR Odyssey system. To detect capsid associated HBV DNA, the membrane were treated with buffer containing 0.5N NaOH and 1.5 M NaCl for 5 minutes and followed by neutralization with buffer containing 1 M TRIS-HCl and 1.5M NaCl for 5 minutes. The viral DNA was detected by hybridization with a α-$^{32}$P-UTP (800 Ci/mmol, Perkin Elmer) labeled minus strand specific full-length HBV riboprobe (Xu et al.).

To analyze the HBV DNA replication intermediates, cells were lysed by adding into each well of the 12-well plates 0.5 ml of lysis buffer containing 10 mM Tris-HCl (pH 8.0), 1 mM EDTA, 1% NP40 and 2% sucrose and incubating at 37° C. for 10 minutes. Cell debris and nuclei were removed by centrifugation and the supernatant was mixed with 130 µl of 35% polyethylene glycol (PEG) 8000 containing 1.5 M NaCl. After 1 hour incubation in ice, viral nucleocapsids were pelleted by centrifugation at 6,000×g for 5 minutes at 4° C., followed by 1 hour digestion at 37° C. in 400 µl of digestion buffer containing 0.5 mg/ml pronase (Calbiochem), 0.5% SDS, 150 mM NaCl, 25 mM Tris-HCl (pH 8.0) and 10 mM EDTA. The digestion mixture was extracted twice with phenol and DNA was precipitated with ethanol, dissolved in TE buffer (10 mM Tris-HCl, pH 8.0; 0.1 mM EDTA). One half of the DNA sample from each well was resolved by electrophoresis into a 1.5% agarose gel. The gel was then subjected to denaturation in a solution containing 0.5 M NaOH and 1.5 M NaCl, followed by neutralization in a buffer containing 1 M Tris-HCl (pH7.4) and 1.5 M NaCl.

DNA was then blotted onto Hybond-XL membrane (GE Health care) in 20×SSC buffer. The HBV DNA replication intermediates were probed with an alpha-$^{32}$P-UTP labeled riboprobe specific for minus strand of HBV genome.

Figure 3:
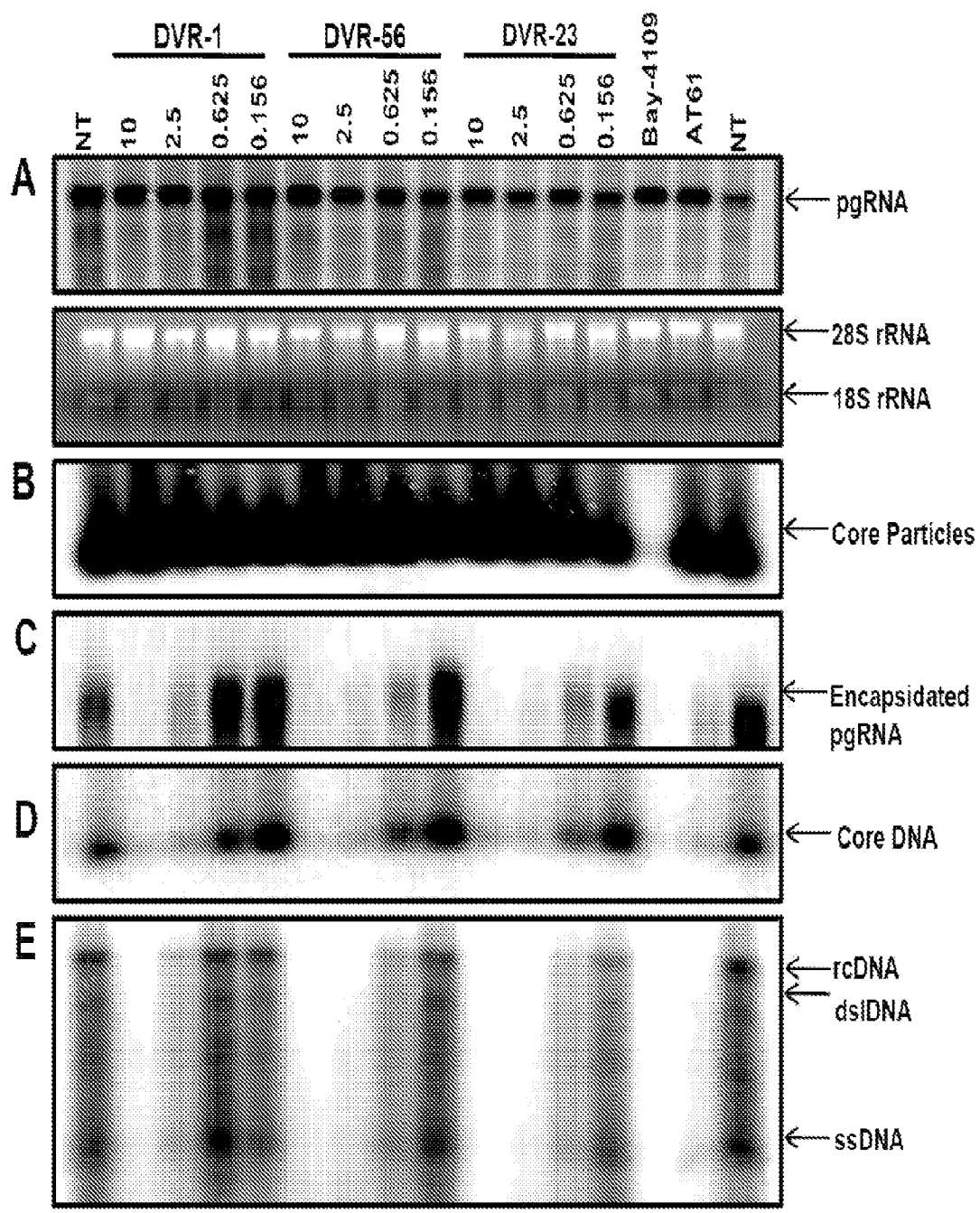
FIG. 3: Antiviral mechanism of the compounds of the present invention. AML12HBV10 cells were left untreated (NT) or treated with the indicated concentrations of the compounds of the disclosure DVR-1, DVR-56 and DVR-23, respectively, for 2 days. Bay-4109 (5 μM) or AT-61 (25 μM) served as positive controls. (A) Intracellular viral RNA was determined by Northern blot hybridization. (B) The total amounts of nucleocapsids were determined by a particle gel assay. (C) Encapsidated pgRNA were extracted and measured by Northern blot. (D) Nucleocapsid-associated HBV DNA was quantified by alkaline-treatment of nucleocapsids on the membrane following the particle gel assay and hybridized with a HBV-specific riboprobe. (E) HBV DNA replication intermediates were extracted and determined by Southern blot hybridizations.

As shown in FIG. 3, DVR-1, DVR-56 and DVR-23 did not affect the amount of viral mRNA (panel A), but dose-dependently reduced the level of encapsidated pgRNA (Panel C). However, consistent with the proposed mechanism, particle gel assay reveled that Bay41-4109 treatment completely abolished capsid formation (panel B) and thus pgRNA encapsidation and DNA synthesis (panels C, D and E), AT-61 treatment did not affect capsid formation (panel B), but dose-dependently reduced the amounts of encapsidated pgRNA (panel C) and the capsid-associated HBV DNA (panels D and E). Similar to AT-61, DVR compounds did not significantly affect capsid formation (panel B), but reduced encapsidated pgRNA and capsid-associated HBV DNA in a dose-dependent manner (panels C, D and E). The above results imply that phenotypically similar with AT-61, the DVR compounds inhibited pgRNA encapsidation into nucleocapsids and resulted in formation of empty capsids. As a consequence, the subsequent HBV DNA replication could not occur.

TABLE 5

Antiviral activity ($EC_{50}$) by dot blot hybridization and cellular toxicity ($CC_{50}$) of compounds of the formula (V):

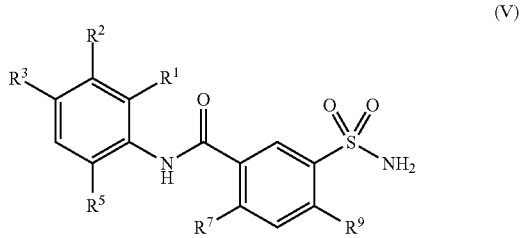

(V)

| Compound Name | $R_1$ | $R_2$ | $R_3$ | $R_5$ | $R_7$ | $R_9$ | $EC_{50}$ (μM) | $CC_{50}$ (μM) |
|---|---|---|---|---|---|---|---|---|
| DVR-16 | H | $CH_3$ | H | H | Cl | H | 6 | >50 |
| DVR-19 | H | $CF_3$ | H | H | H | F | 9 | >50 |
| DVR-21 | H | $CF_3$ | H | Cl | H | F | 6.8 | >50 |
| DVR-22 | H | H | H | H | H | H | 8 | >50 |

TABLE 6

Antiviral activity ($EC_{50}$) by dot blot hybridization and cellular toxicity ($CC_{50}$) of compounds of the formula (VI):

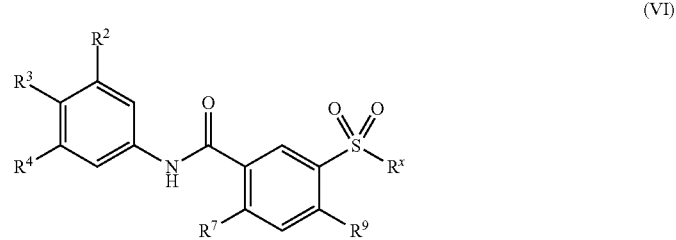

(VI)

| Compound | $R^2$ | $R^3$ | $R^4$ | $R^7$ | $R^9$ | $R^x$ | $EC_{50}$ (μM) | $CC_{50}$ (μM) |
|---|---|---|---|---|---|---|---|---|
| DVR-23 | F | F | H | F | H | (NH-propyl) | 0.39 | >50 |
| DVR-24 | H | H | H | H | H | (NEt₂) | 8 | >50 |
| DVR-25 | F | F | H | F | H | (NEt₂) | 10.5 | >50 |
| DVR-26 | $CH_3$ | H | H | Cl | H | (NEt₂) | 3 | >50 |

TABLE 6-continued

Antiviral activity (EC$_{50}$) by dot blot hybridization and cellular toxicity (CC$_{50}$) of compounds of the formula (VI):

(VI)

| Compound | R$^2$ | R$^3$ | R$^4$ | R$^7$ | R$^9$ | R$^x$ | EC$_{50}$ (μM) | CC$_{50}$ (μM) |
|---|---|---|---|---|---|---|---|---|
| DVR-27 | H | Cl | H | H | H | -N(Et)$_2$ (diethylamino) | 25 | >50 |
| DVR-34 | F | F | H | F | H | -NH-allyl | 4 | >50 |
| DVR-42 | F | F | H | F | H | -N(propyl)$_2$ | 17.5 | >50 |
| DVR-43 | F | F | H | F | H | -NH-cycloheptyl | 0.39 | >50 |
| DVR-44 | H | CH$_3$ | H | F | H | -NH-cycloheptyl | 25 | >50 |
| DVR-45 | F | F | H | F | H | -NH-cyclohexyl | 0.8 | >50 |
| DVR-47 | H | H | H | Br | H | -NH-cyclohexyl | 3.7 | >50 |
| DVR-51 | H | F | H | H | Cl | -NH-cyclohexyl | 2.1 | >50 |
| DVR-52 | H | H | H | H | CH$_3$ | -NH-cyclohexyl | 4 | >50 |

TABLE 6-continued

Antiviral activity (EC$_{50}$) by dot blot hybridization and cellular toxicity (CC$_{50}$) of compounds of the formula (VI):

(VI)

| Compound | R$^2$ | R$^3$ | R$^4$ | R$^7$ | R$^9$ | R$^X$ | EC$_{50}$ (μM) | CC$_{50}$ (μM) |
|---|---|---|---|---|---|---|---|---|
| DVR-53 | F | F | H | H | F | 2-methylcyclohexylamino | 27.1 | >50 |
| DVR-55 | H | H | H | H | H | cyclopentylamino | 1 | >50 |
| DVR-56 | F | F | H | F | H | cyclopentylamino | 0.39 | >50 |
| DVR-57 | H | F | H | F | H | cyclopentylamino | 21.3 | >50 |
| DVR-61 | CH$_3$ | H | CH$_3$ | F | H | cyclopentylamino | 4.5 | >50 |
| DVR-62 | CH$_3$ | H | H | H | F | cyclopentylamino | 2.8 | >50 |
| DVR-63 | Cl | H | Cl | F | H | cyclopentylamino | 10.2 | >50 |
| DVR-64 | H | H | H | H | H | furan-2-ylmethylamino | 3 | >50 |
| DVR-65 | Cl | F | H | F | H | furan-2-ylmethylamino | 5 | >50 |
| DVR-66 | F | H | H | F | H | furan-2-ylmethylamino | 2.9 | >50 |

TABLE 6-continued
Antiviral activity (EC$_{50}$) by dot blot hybridization and cellular toxicity (CC$_{50}$) of compounds of the formula (VI):
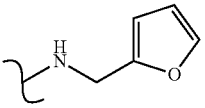
(VI)
| Compound | R$^2$ | R$^3$ | R$^4$ | R$^7$ | R$^9$ | R$^X$ | EC$_{50}$ (μM) | CC$_{50}$ (μM) |
|---|---|---|---|---|---|---|---|---|
| DVR-68 | Cl | H | Cl | F | H | 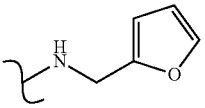 | 11.4 | >50 |
| DVR-69 | CH$_3$ | H | H | H | F | 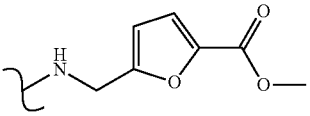 | 3.1 | >50 |
| DVR-70 | H | H | H | Cl | H | 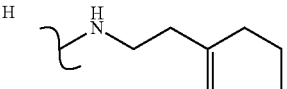 | 11 | >50 |
| DVR-73 | Cl | H | H | F | H | 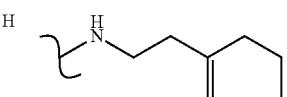 | 10.2 | >50 |
| DVR-74 | CH$_3$ | H | CH$_3$ | F | H |  | 25 | — |
| DVR-75 | H | H | H | H | H |  | 4.1 | — |
| DVR-77 | Cl | H | H | H | F | 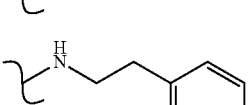 | 11.1 | — |
| DVR-82 | F | F | H | F | H | 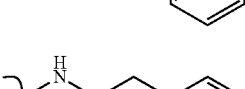 | 2 | >50 |
| DVR-83 | Cl | H | H | F | H | 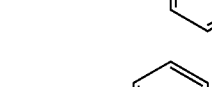 | 3 | >50 |
| DVR-87 | Cl | F | H | F | H |  | 3.1 | >50 |

TABLE 6-continued

Antiviral activity (EC$_{50}$) by dot blot hybridization and cellular toxicity (CC$_{50}$) of compounds of the formula (VI):

(VI)

| Compound | R$^2$ | R$^3$ | R$^4$ | R$^7$ | R$^9$ | R$^X$ | EC$_{50}$ (μM) | CC$_{50}$ (μM) |
|---|---|---|---|---|---|---|---|---|
| DVR-89 | H | H | H | Cl | H | benzyl-NH- | 1.2 | >50 |
| DVR-91 | H | Cl | H | F | H | 3,4-dimethoxyphenethyl-NH- | 16.8 | >50 |
| DVR-92 | F | F | H | F | H | 2-chlorobenzyl-NH- | 1 | >50 |
| DVR-93 | H | Cl | H | H | F | 2-chlorobenzyl-NH- | 4.8 | >50 |
| DVR-94 | CH$_3$ | H | H | F | H | 4-methoxyphenyl-NH- | 40 | >50 |
| DVR-96 | CH$_3$ | H | H | F | H | 4-fluorophenyl-NH- | 14 | >50 |
| DVR-98 | H | Cl | H | H | H | 3-fluorophenyl-NH- | 45 | >50 |
| DVR-100 | H | Cl | H | H | H | 2-methylphenyl-NH- | 20 | >50 |

TABLE 6-continued

Antiviral activity (EC$_{50}$) by dot blot hybridization and cellular toxicity (CC$_{50}$) of compounds of the formula (VI):

(VI)

| Compound | R$^2$ | R$^3$ | R$^4$ | R$^7$ | R$^9$ | R$^X$ | EC$_{50}$ (μM) | CC$_{50}$ (μM) |
|---|---|---|---|---|---|---|---|---|
| DVR-101 | H | H | H | H | H | NH-(3-methylphenyl) | 32 | >50 |
| DVR-102 | H | H | H | H | H | NH-(2-methylphenyl) | 15 | >50 |
| DVR-103 | F | F | H | H | F | N(Et)(CH$_2$Ph) | 5 | >50 |
| DVR-104 | F | F | H | F | H | azepan-1-yl | 0.6 | >50 |
| DVR-107 | H | H | H | H | CH$_3$ | piperidin-1-yl | 4 | >50 |
| DVR-108 | H | F | H | H | Cl | piperidin-1-yl | 2.1 | >50 |
| DVR-115 | F | H | H | H | Cl | morpholin-4-yl | 25 | >50 |
| DVR-117 | H | H | H | H | Cl | thiomorpholin-4-yl | 4.5 | >50 |

TABLE 7

Antiviral activity (EC$_{50}$) by dot blot hybridization and cellular toxicity (CC$_{50}$) of compounds of the formula (II):

(II)

| Compound | R$^x$ | EC$_{50}$ (µM) | CC$_{50}$ (µM) |
|---|---|---|---|
| DVR-23 | -NH-propyl | 0.39 | >50 |
| DVR-25 | -N(ethyl)$_2$ | 10.5 | >50 |
| DVR-34 | -NH-allyl | 4 | >50 |
| DVR-42 | -N(propyl)$_2$ | 17.5 | >50 |
| DVR-43 | -NH-cycloheptyl | 0.39 | >50 |
| DVR-104 | azepan-1-yl | 0.6 | >50 |
| DVR-45 | -NH-cyclohexyl | 0.8 | >50 |
| DVR-56 | -NH-cyclopentyl | 0.39 | >50 |
| DVR-82 | -NH-CH$_2$CH$_2$-phenyl | 2 | >50 |
| DVR-92 | -NH-CH$_2$-(2-chlorophenyl) | 1 | >50 |

TABLE 8
Antiviral activity (EC$_{50}$) by dot blot hybridization and cellular toxicity (CC$_{50}$) of compounds of the formula (III):
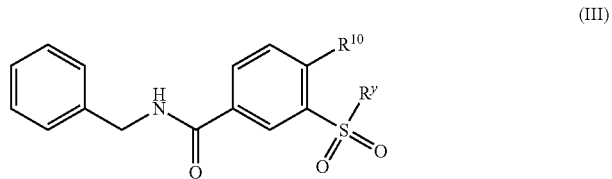
(III)
| Compound | R$^{10}$ | R$^y$ | EC$_{50}$ (μM) | CC$_{50}$ (μM) |
|---|---|---|---|---|
| DVR-01 | Cl | azepane | 4 | >50 |
| DVR-02 | Cl | piperidine | 7 | >50 |
| DVR-08 | CH$_3$ | 4-methylpiperidine | 44 | >50 |
| DVR-09 | CH$_3$ | benzylamino | 33 | >50 |
| DVR-10 | H | 3-carboxyphenylamino | 49 | >50 |
| DVR-11 | Br | diethylamino | 112 | >50 |

TABLE 9

Antiviral activity (EC$_{50}$) by dot blot hybridization and cellular toxicity (CC$_{50}$) of compounds of the formula (IV):

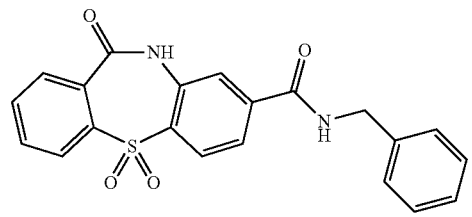 [SMILES: O=C(NCc1ccccc1)c1ccc2c(c1)NC(=O)c1ccccc1S2(=O)=O]

(IV)

| Compound | EC$_{50}$ (μM) | CC$_{50}$ (μM) |
|---|---|---|
|  | 8 | >50 |

TABLE 10

Antiviral activity of exemplary compounds of the formula (II) in AML12HBV10 and HepDES19 cells:

(II)

| Compound | R$^x$ | AML12HBV10 | | HepDES19 | | |
|---|---|---|---|---|---|---|
| | | EC$_{50}$ | CC$_{50}$ | EC$_{50}$ | EC$_{90}$ | CC$_{50}$ |
| DVR-43 | N-cycloheptyl | 0.39 | >50 | 0.72 | 1.33 | 45 |
| DVR-45 | N-cyclohexyl | 0.8 | >50 | 0.48 | 2.11 | >50 |
| DVR-92 | N-CH$_2$-(2-Cl-phenyl) | 1 | >50 | 0.98 | 2.9 | >50 |
| DVR-56 | N-cyclopentyl | 0.39 | >50 | 0.42 | 1.85 | >50 |

TABLE 10-continued

Antiviral activity of exemplary compounds of the formula (II) in AML12HBV10 and HepDES19 cells:

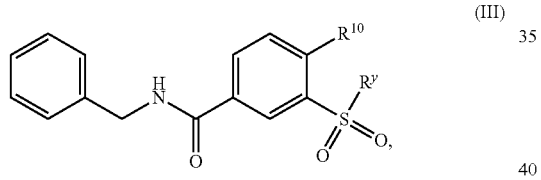

| Compound | R$^x$ | AML12HBV10 | | HepDES19 | | |
|---|---|---|---|---|---|---|
| | | EC$_{50}$ | CC$_{50}$ | EC$_{50}$ | EC$_{90}$ | CC$_{50}$ |
| DVR-23 | | 0.39 | >50 | 0.28 | 0.86 | >50 |
| DVR-104 | | 0.6 | >50 | 0.97 | 3.11 | >50 |

What is claimed is:

1. A pharmaceutical composition comprising at least one pharmaceutically acceptable carrier, at least one compound of formula (III):

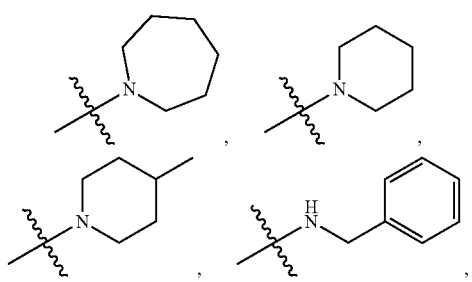

wherein:
R$^{10}$ is selected from the group consisting of H, CH$_3$, Cl and Br;
R$^y$ is selected from the group consisting of

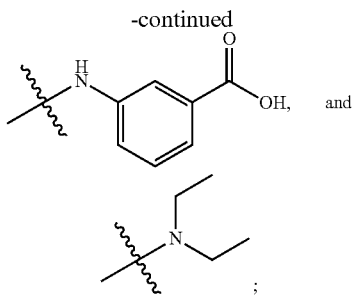

or a pharmaceutically acceptable salt thereof,
and at least one additional agent that treats Hepatitis B virus (HBV) infection.

2. A pharmaceutical composition comprising at least one pharmaceutically acceptable carrier, at least one compound selected from the group consisting of:
3-(Azepane-1-sulfonyl)-N-benzyl-4-chloro-benzamide,
N-Benzyl-4-chloro-3-(piperidine-1-sulfonyl)-benzamide,
N-Benzyl-4-methyl-3-(4-methyl-piperidine-1-sulfonyl)-benzamide,
N-Benzyl-3-benzylsulfamoyl-4-methyl-benzamide,
3-(3-Benzylcarbamoyl-benzenesulfonylamino)-benzoic acid,
N-Benzyl-4-bromo-3-diethylsulfamoyl-benzamide,
any pharmaceutically acceptable salt thereof, and any mixtures thereof; and at least one additional agent that treats Hepatitis B virus (HBV) infection.

* * * * *